US007901678B2

(12) United States Patent
Nakahara et al.

(10) Patent No.: US 7,901,678 B2
(45) Date of Patent: Mar. 8, 2011

(54) MEDICINAL COMPOSITIONS CONTAINING FC RECEPTOR γ CHAIN ACTIVATOR

(75) Inventors: Jin Nakahara, Tokyo (JP); Hiroaki Asou, Tokyo (JP); Sadakazu Aiso, Tokyo (JP)

(73) Assignee: Keio University, Tokyo (JP)

( * ) Notice: Subject to any disclaimer, the term of this patent is extended or adjusted under 35 U.S.C. 154(b) by 340 days.

(21) Appl. No.: 11/451,488

(22) Filed: Jun. 13, 2006

(65) Prior Publication Data

US 2007/0178083 A1 Aug. 2, 2007

Related U.S. Application Data

(63) Continuation of application No. 10/485,614, filed as application No. PCT/JP02/07378 on Jul. 22, 2002, now abandoned.

(30) Foreign Application Priority Data

Jul. 30, 2001 (JP) ................................. 2001-229553

(51) Int. Cl.
*A61K 39/395* (2006.01)
(52) U.S. Cl. .................................. 424/133.1; 424/144.1
(58) Field of Classification Search .................. None
See application file for complete search history.

(56) References Cited

U.S. PATENT DOCUMENTS

| 5,985,276 | A | 11/1999 | Lindhofer et al. |
| 6,210,668 | B1 | 4/2001 | Lindhofer et al. |
| 6,551,592 | B2 | 4/2003 | Lindhofer et al. |

FOREIGN PATENT DOCUMENTS

| JP | 9-145714 | 6/1997 |
| JP | 10-179151 | 7/1998 |
| JP | 10-182487 | 7/1998 |
| JP | 2000-135089 | 5/2000 |
| JP | 2001-13448 | 5/2001 |
| JP | 2001-133448 | 5/2001 |

OTHER PUBLICATIONS

Iruretagoyena et al. Activating and inhibitory Fcgamma receptors can differentially modulate T cell-mediated autoimmunity. . Eur J Immunol. Aug. 2008;38(8):2241-50.*
Noseworthy et al . IV immunoglobulin does not reverse established weakness in MS.. Neurology. Oct. 24, 2000;55(8):1135-43.*
Stangel et al. Placebo controlled pilot trial to study the remyelinating potential of intravenous immunoglobulins in multiple sclerosis. J. Neurol Neurosurg Psychiatry 2000, 68:89-92.*
Fazekas et al. Randomised placebo-controlled trial of monthly intravenous immunoglobulin therapy in relapsing-remitting multiple sclerosis. Lancet 1997, 349:589-93.*
Cochlovius et al Therapeutic Antibodies After years of promise, magic bullets appear to be on the upswing. Modern Drug Discovery, 2003, pp. 33-34 and 37-38.*
Umemori et al.Initial events of myelination involve Fyn tyrosine kinase signalling. Nature. 1994, 367:572-576.*
Nakahara et al. Abnormal expression of TIP30 and arrested nucleocytoplasmic transport within oligodendrocyte precursor cells in multiple sclerosis. J Clin Invest. 2009;119(1):169-181.*
Esther et al. K. Neuropathol. Exp. Neurol. 2005, 65:304-311.
Hartung et al. J. Neurol. 2005, 252(Supp. 5):V/30-V/37.
Graziano et al. The Journal of Immunology, 1995, 155:4996-5002.
Nakahara et al. Developmental Cell, 2003, 4:841-852.
Subramaniam Sriram, et al., "Experimental Allergic Encephalomyelitis: A Misleading Model of Multiple Sclerosis", American Neurological Association, Annals of Neurology vol. 58, No. 6, Dec. 2005, pp. 939-945.
Jin Nakahara, et al., "Fc Receptor-Positive Cells in Remyelinating Multiple Sclerosis Lesions", J Neuropathol Exp Neurol, vol. 65, No. 6, Jun. 2006, pp. 582-591.
John D. Cahoy, et al., "A Transcriptome Database for Astrocytes, Neurons, and Oligodendrocytes: A New Resource for Understanding Brain Development and Function", The Journal of Neuroscience, Jan. 2, 2008, pp. 264-278.
J. D. Cahoy, et al., "A Transcriptome Database for Astrocytes, Neurons, and Oligodendrocytes: A New Resource for Understanding Brain Development and Function", Online Supplemental data for J Neurosci 28: 264-78 (2008), 1 page.
Christopher Lock, et al., "Gene-microarray analysis of multiple sclerosis lesions yields new targets validated in autoimmune encephalomyelitis", Nature Medicine, vol. 8, No. 5, May 2002, pp. 500-508.
Jin Nakahara, et al., "Signaling via Immunoglobulin Fc Receptors Induces Oligodendrocyte Precursor Cell Differentiation", Developmental Cell, vol. 4, Jun. 2003, pp. 841-852.
Christopher B. Lock, et al., "Gene microarray analysis of multiple sclerosis lesions", Trends in Molecular Medicine, vol. 9, No. 12, Dec. 2003, pp. 535-541.
Chika Seiwa, et al., Restoration of FcRγ/Fyn Signaling Repairs Central Nervous System Demyelination, Journal of Neuroscience Research, 2007, pp. 954-966. Otto Hommes, et al., "IVIG trials in MS. Is albumin a placebo?", J. Neurol (2009), 256: 268-270.
Jacqueline T. Chen, et al., "Magnetization Transfer Ratio Evolution with Demyelination and Remyelination in Multiple Sclerosis Lesions", Annals of Neurology, vol. 63, No. 2, Feb. 2008; 254-262.
Sha Mi, et al., "LINGO-1 negatively regulates myelination by oligodendrocytes", Nature Neuroscience, vol. 8, No. 6, Jun. 2005; 745-751.
Sha Mi, et al., "Promotion of Central Nervous System Remyelination by Induced Differentiation of Oligodendrocyte Precursor Cells", Annals of Neurology, vol. 65, No. 3, Mar. 2009; 304-315.

(Continued)

Primary Examiner — Maher M Haddad
(74) Attorney, Agent, or Firm — Oblon, Spivak, McClelland, Maier & Neustadt, L.L.P.

(57) ABSTRACT

The present invention provides pharmaceutical compositions composing, as an active ingredient, a substance capable of activating the γ chain of Fc receptors (FcRγ) (provided that the substance is not an immunoglobulin for intravenous injection), and agents for stimulating myelinogenesis. The invention also provides agents for stimulating the differentiation of oligodendroglial precursor cells, agents for activating Fyn tyrosine kinase, and agents for stimulating the expression of myelin basic protein, all comprising a substance capable of activating FcRγ as an active ingredient. Further, the invention provides a method of detecting myelinogenetic oligodendroglias or precursor cells thereof which comprises using the expression of FcRγ in oligodendroglias or precursor cells thereof as an indicator.

19 Claims, 29 Drawing Sheets

OTHER PUBLICATIONS

Sha-Mi, "LINGO-1 antagonist promotes spinal cord remyelination and axonal integrity in MOG-induced experimental autoimmune encephalomyelitis", Nature Medicine, vol. 13, No. 10, Oct. 2007; 1228-1233.

Heather A. Arnett, et al., "bHLH Transcription Factor Olig1 is Required to Repair Demyelinated Lesions in the CNS" Science, vol. 306, pp. 2111-2115, 2004.

Signe Humle Jorgensen, et al., "Intravenous immunoglobulin treatment of multiple sclerosis and its animal model, experimental autoimmune encephalomyelitis", Journal of Neurological Sciences, vol. 233, pp. 61-65, 2005.

Felix Schlachetzki, et al., "Expression of the neonatal Fc receptor (FcRn) at the blood-brain barrier", Journal of Neurochemistry, vol. 81, pp. 203-206, 2002.

Glenn K. Matsushima, et al., "The Nuorotoxicant, Cuprizone, as a Model to Study Demyelination and Remyelination in the Central Nervous System", Brain Pathology 11: 107-116 (2001).

Markus Kipp, et al., "The cuprizone animal model: new insights into an old story", Acta Neuropathol (2009) 118: 723-736.

Sha Mi, et al., "LINGO-1 and its role in CNS repair", The International Journal of Biochemistry & Cell Biology, 40 (2008), pp. 1971-1978.

* cited by examiner

FIG. 1
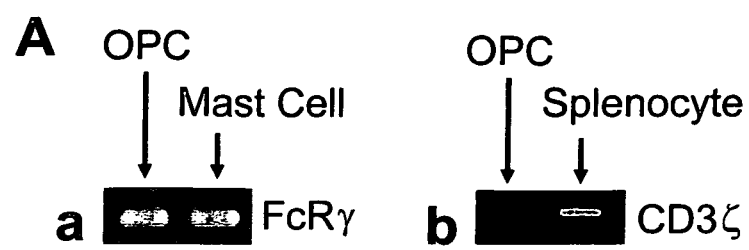
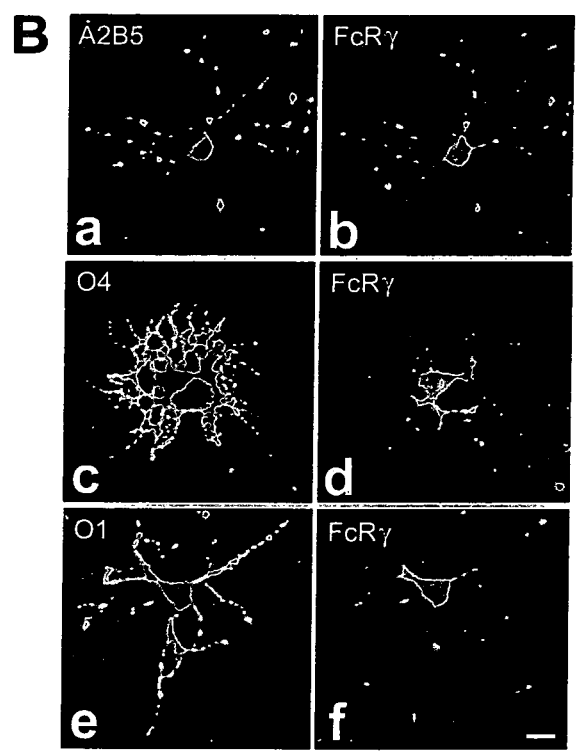
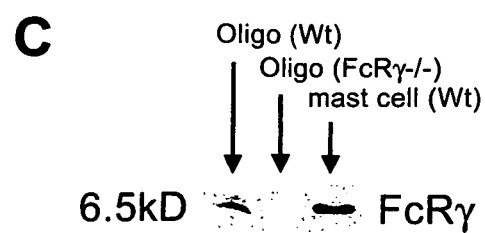

FIG. 2 a, b, c
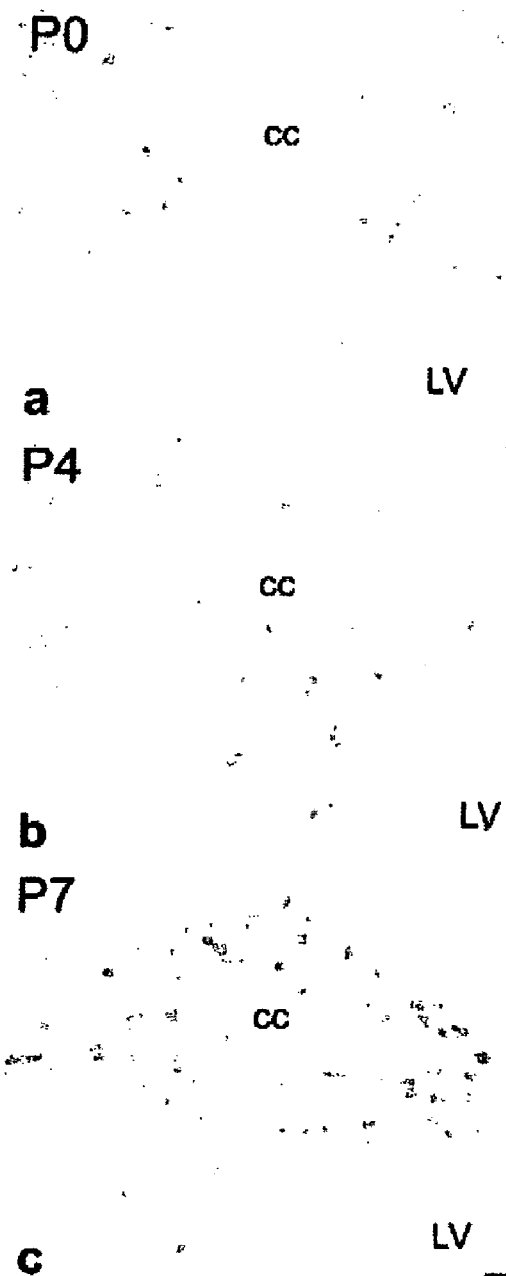

FIG. 2 d, e, f
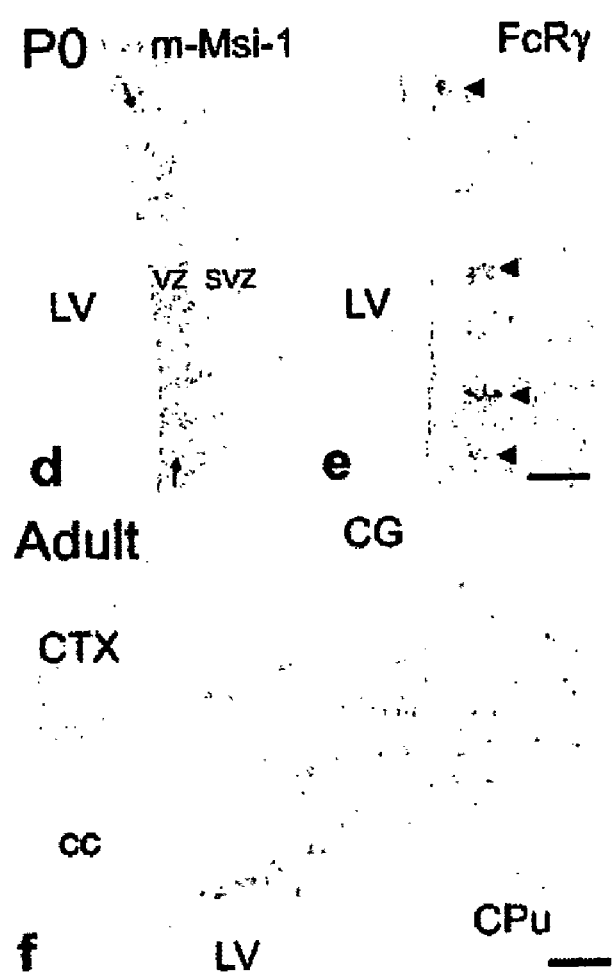

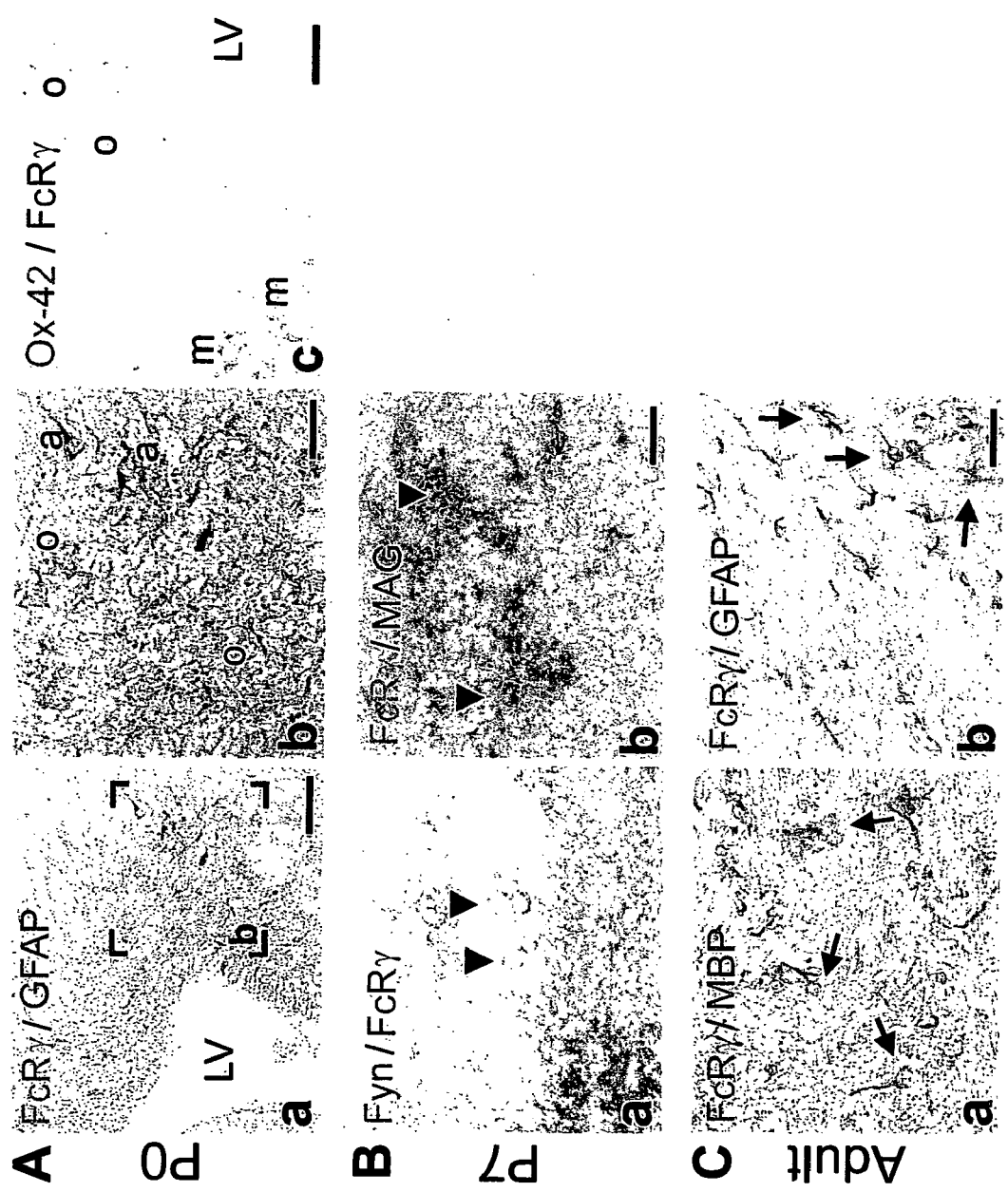
FIG. 3 A, B, C

FIG. 5 B, C
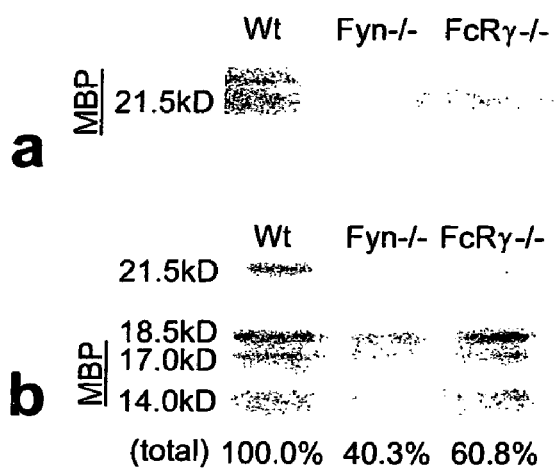
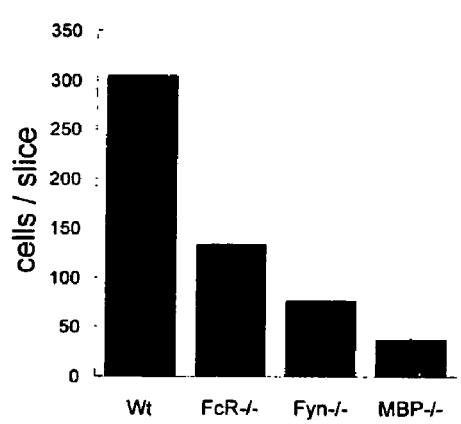

FIG. 6 B
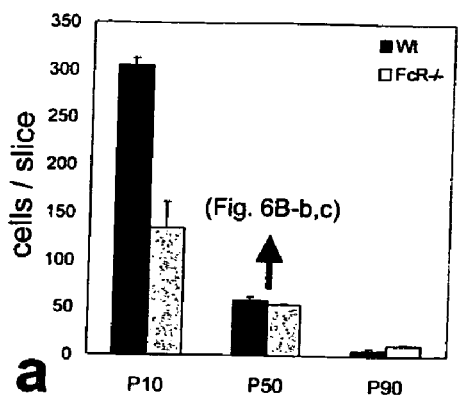
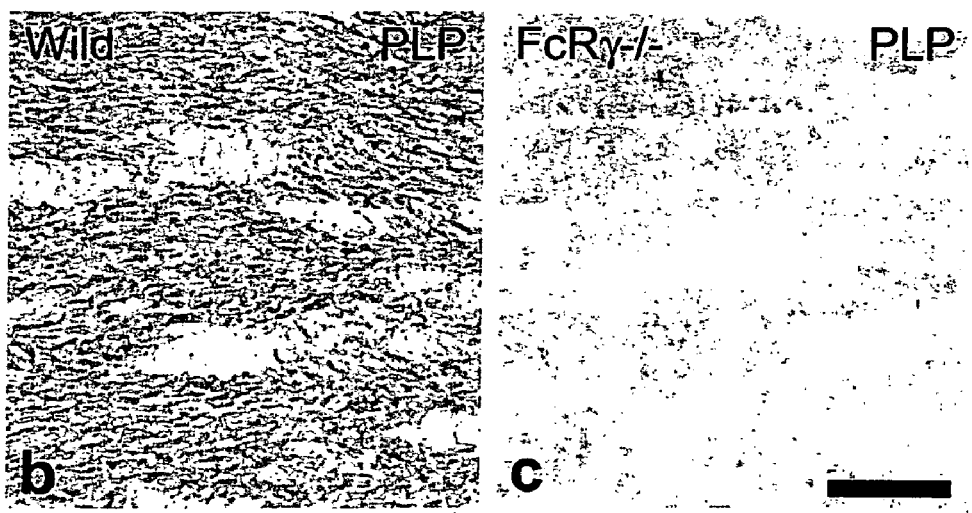

FIG. 7 A, B
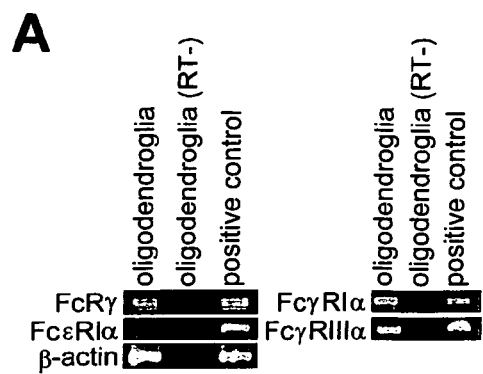
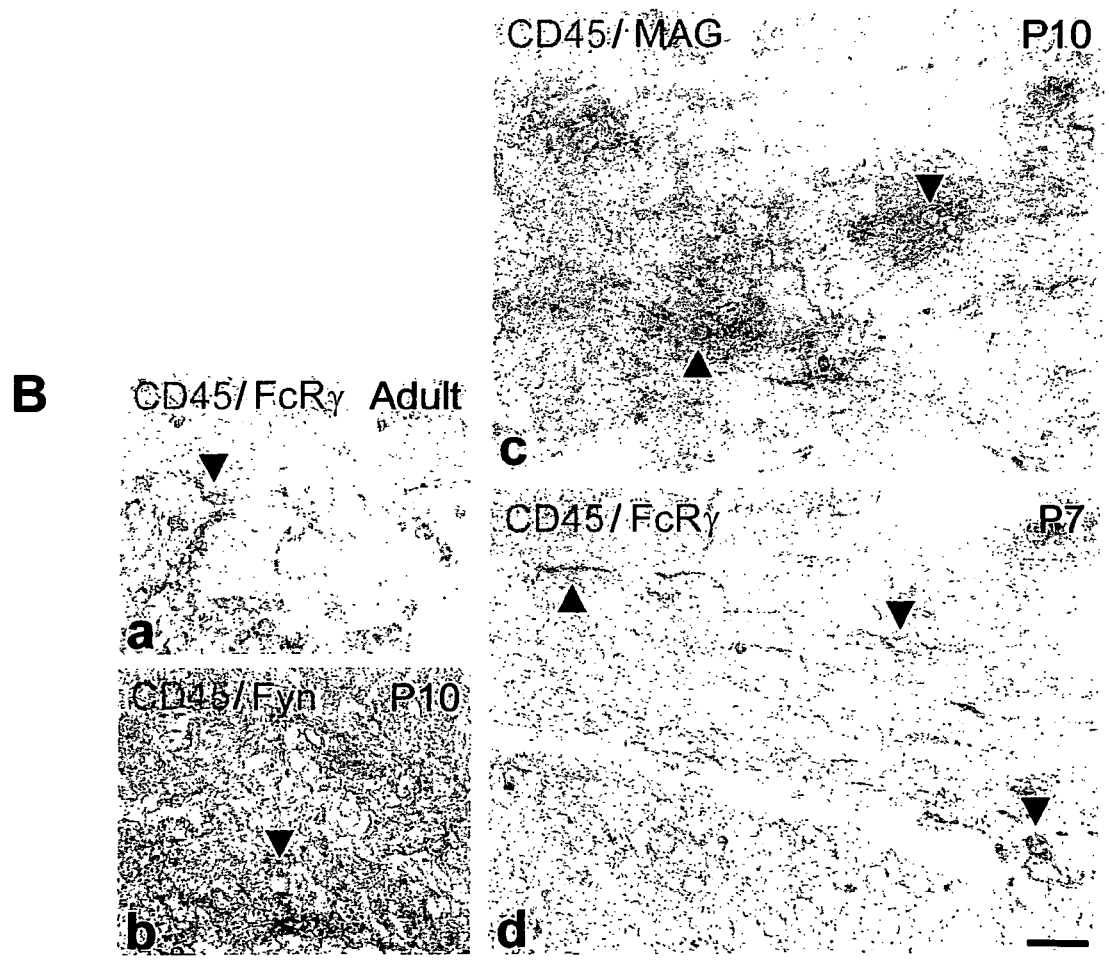

FIG. 10 a, b, c, d
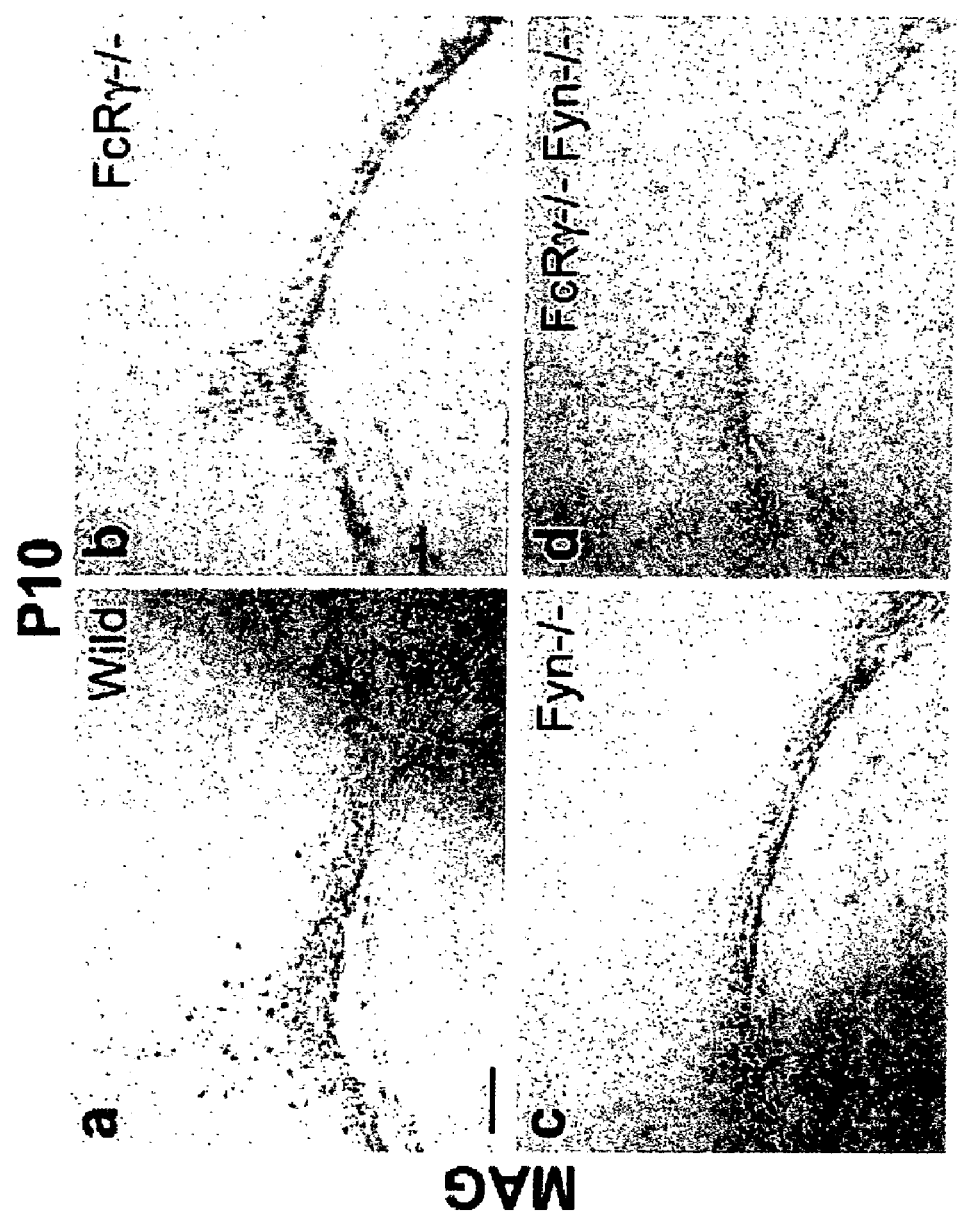

FIG. 10 e, f
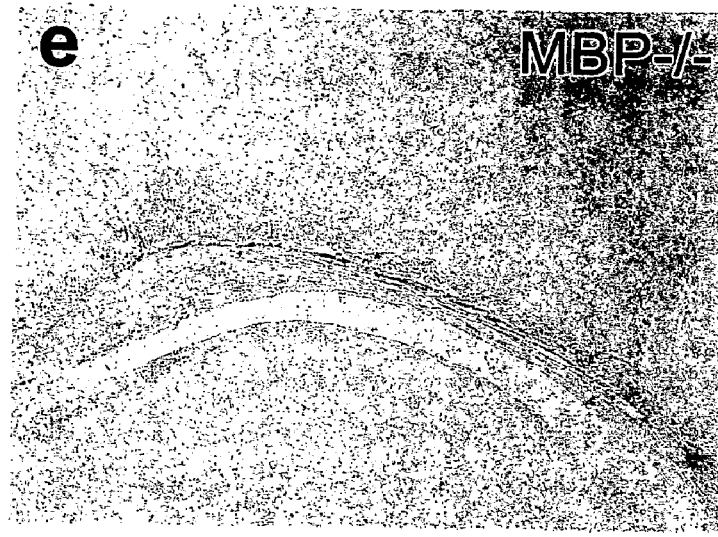
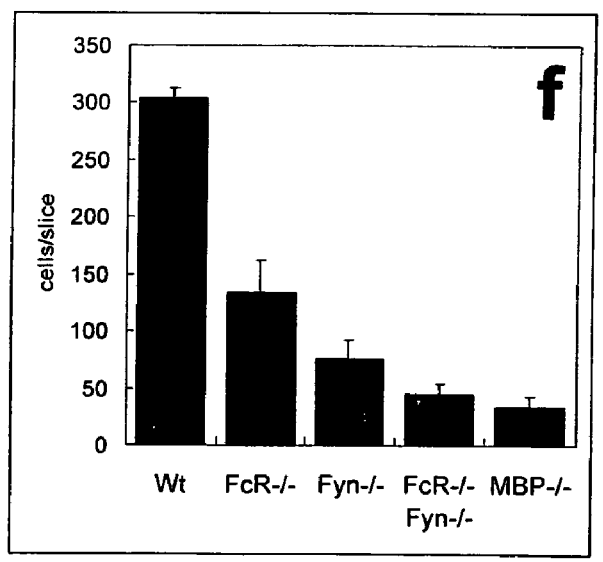

FIG. 11 a, e
Wild P1.5M

FIG. 11 b, f
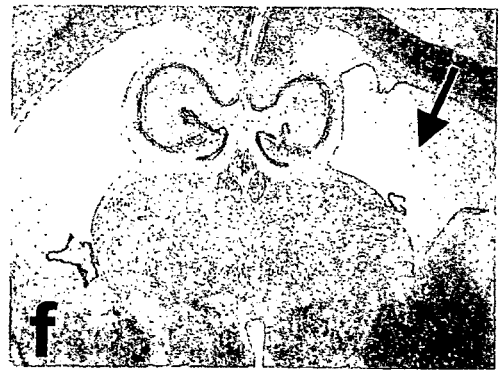

FIG. 11 c, g
FcRγ-/-
Wild P10

FIG. 11 d, h
FcRγ-/- Fyn-/-
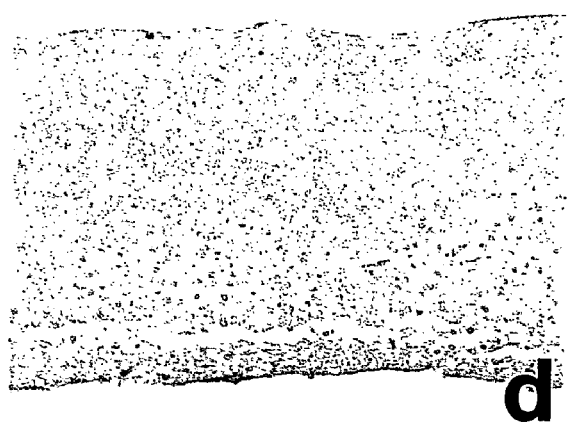
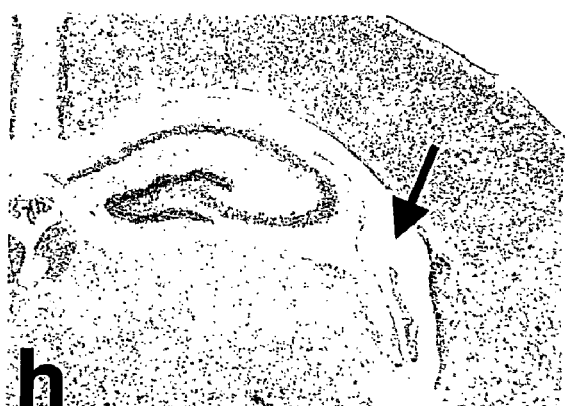
FcRγ-/- Fyn-/- P10

FIG. 12 a, b, c
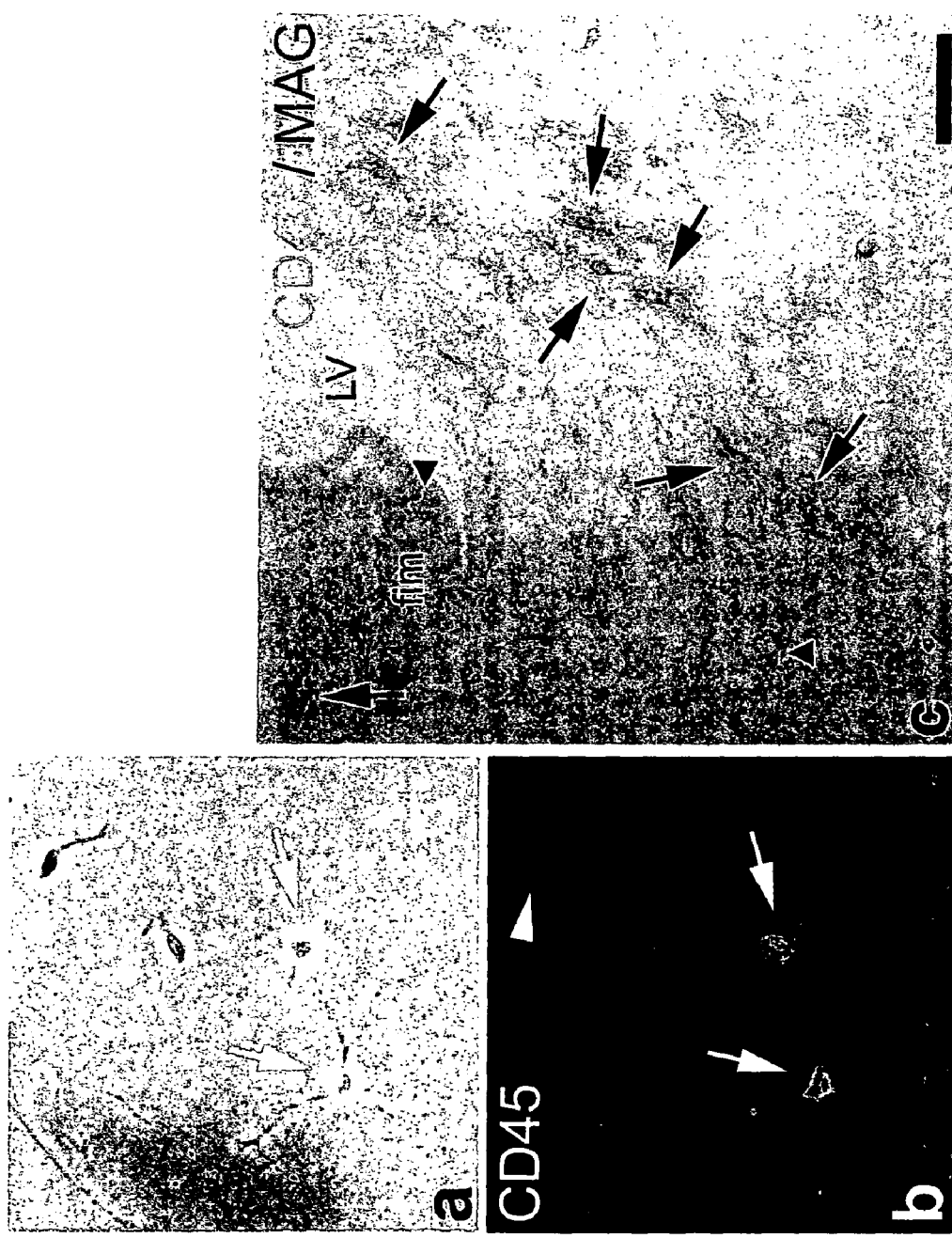

FIG. 12 d, e
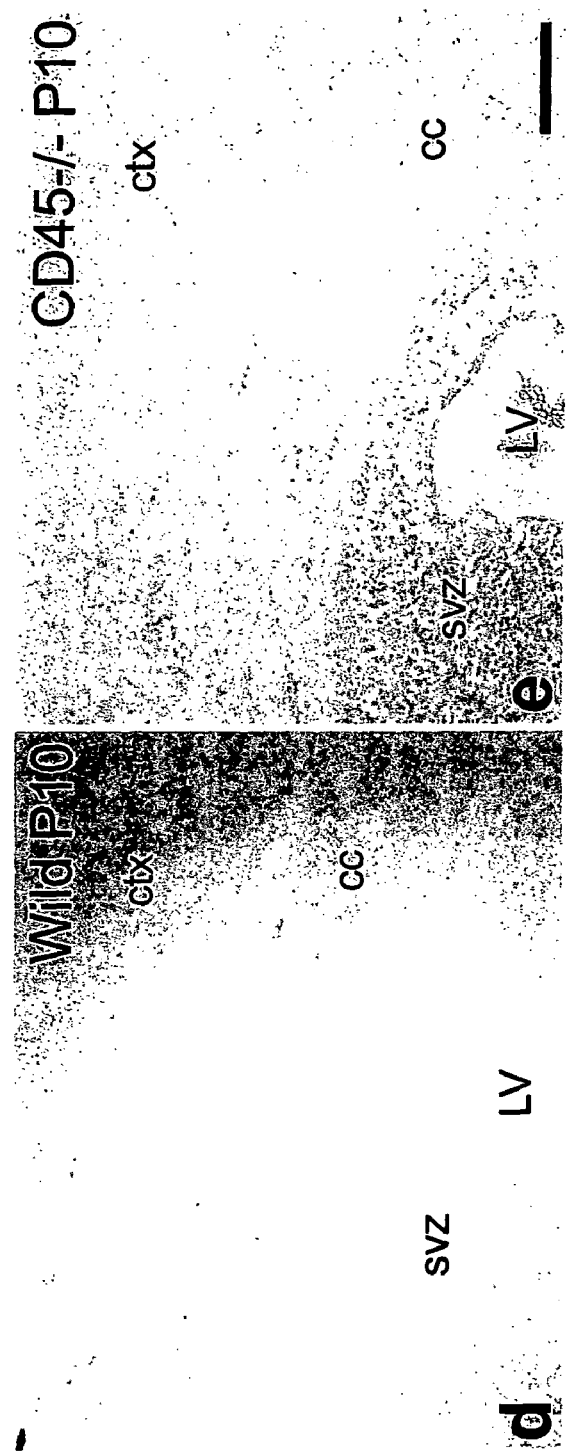

FIG. 13 a, b, c
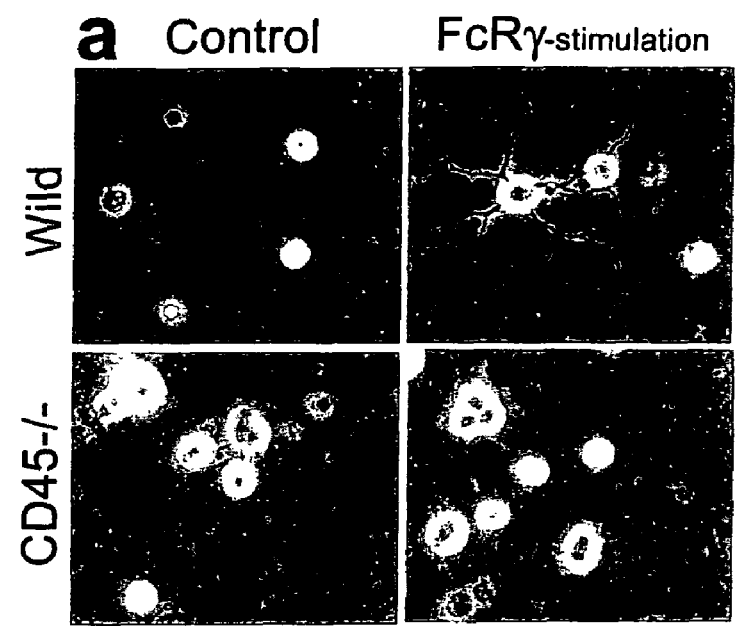
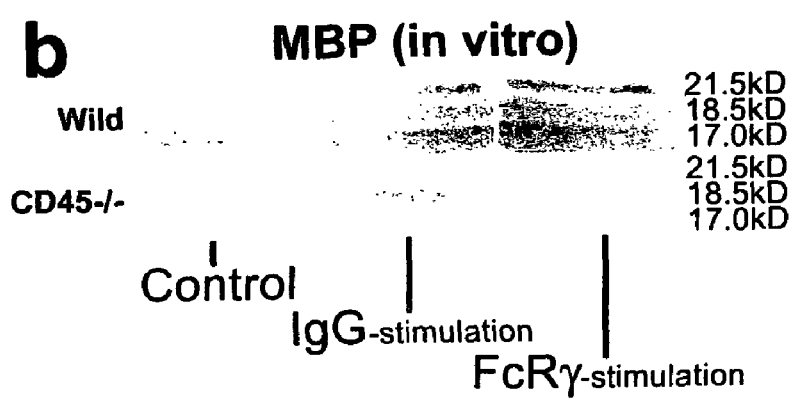
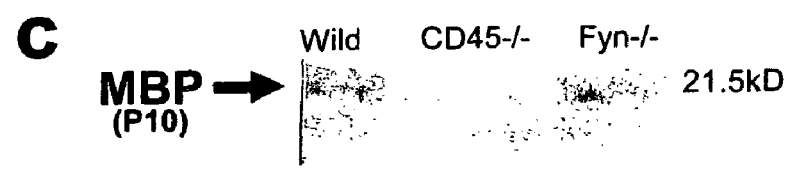

FIG. 13 d, e, f, g, h
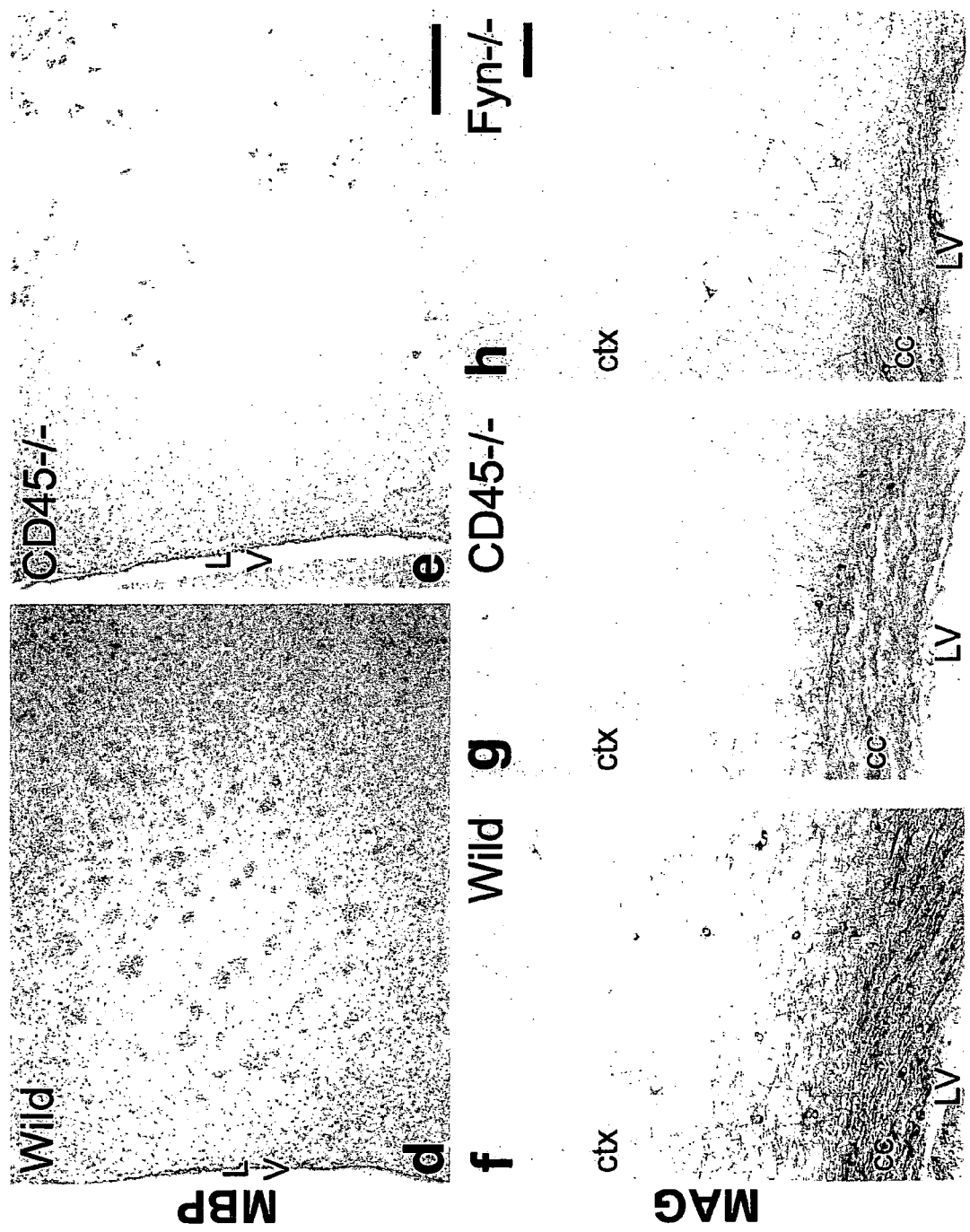

FIG. 14
P1.5M / MBP
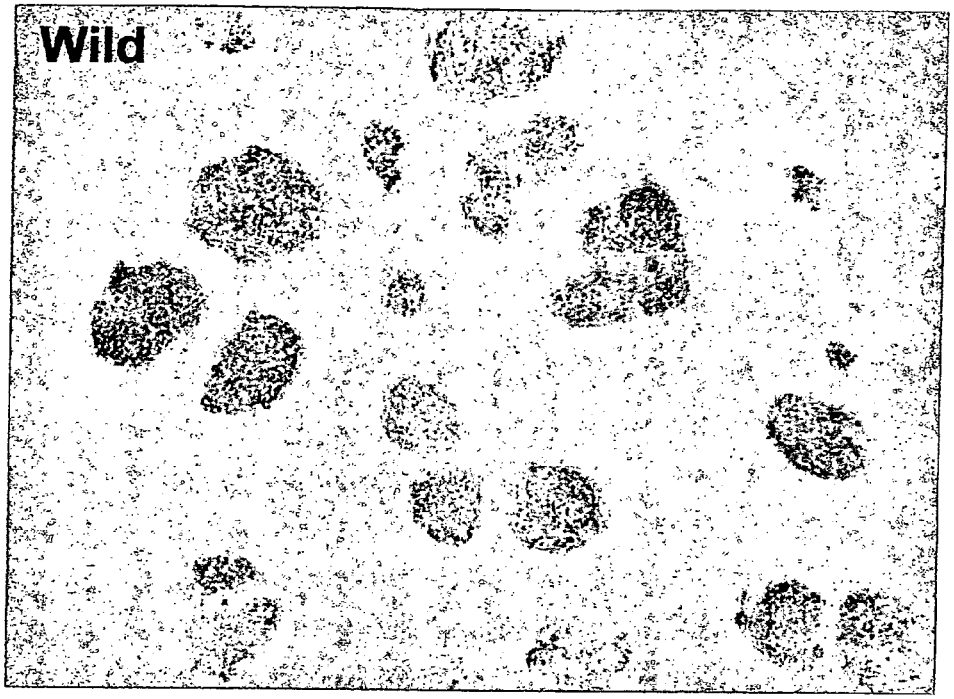

FIG. 15
MAG
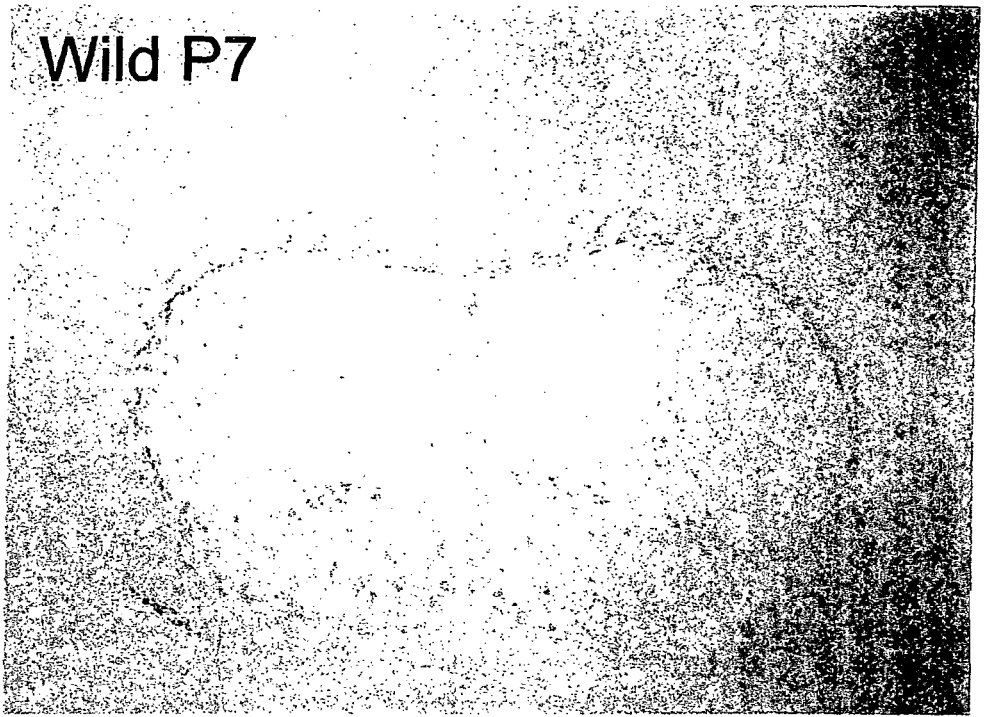
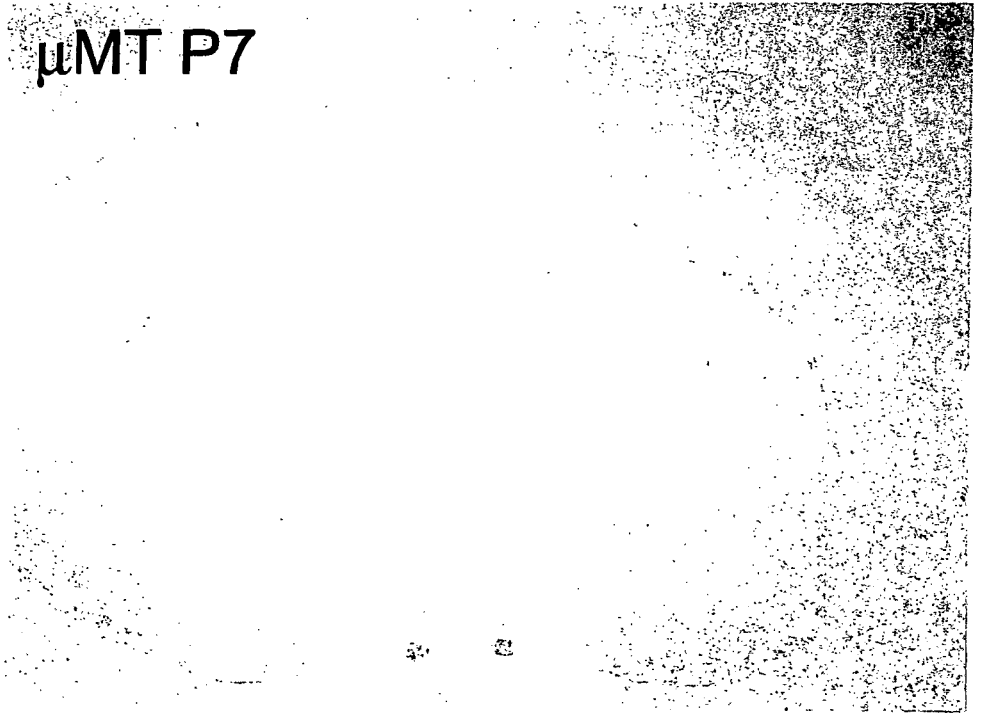

FIG. 16
MAG
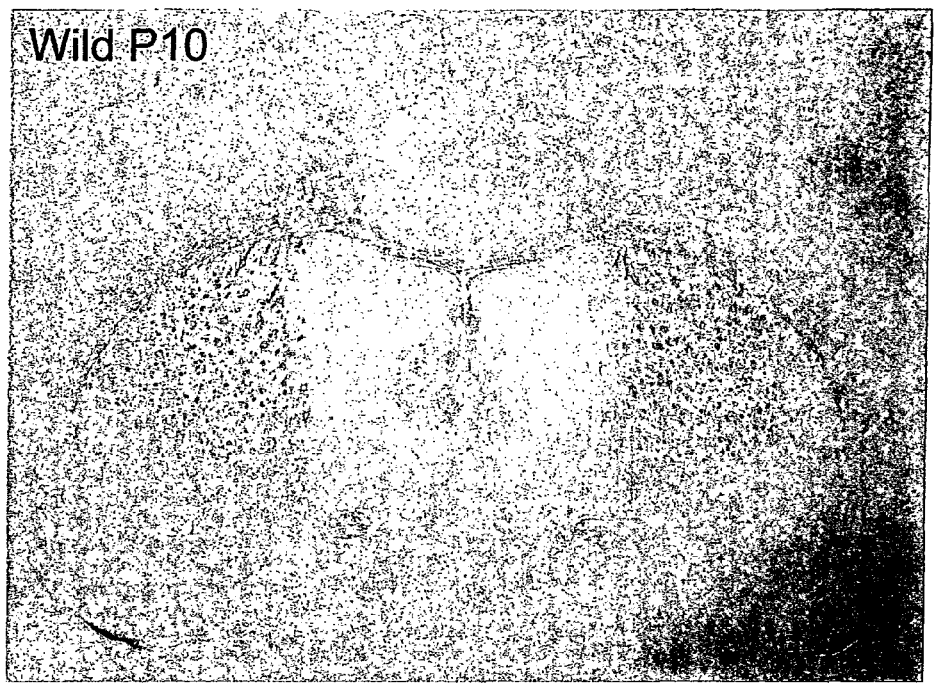
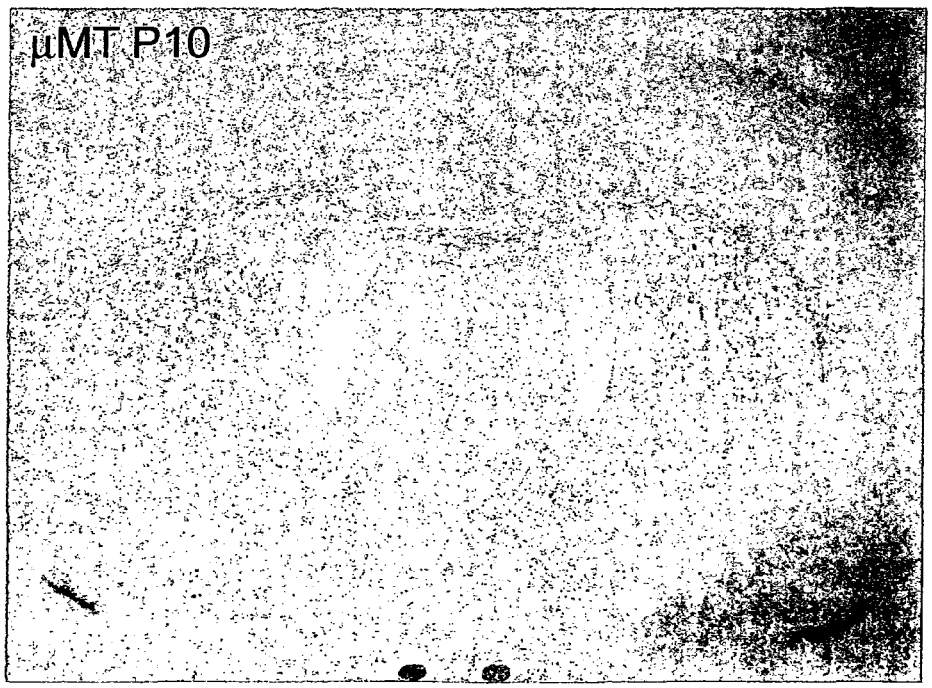

FIG. 17
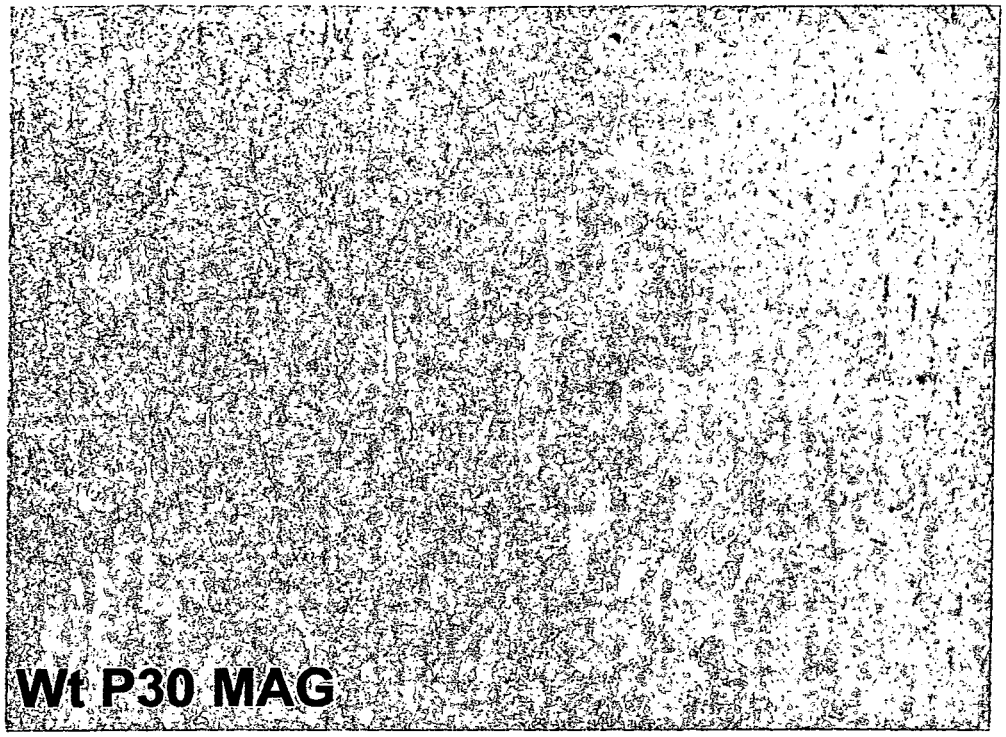
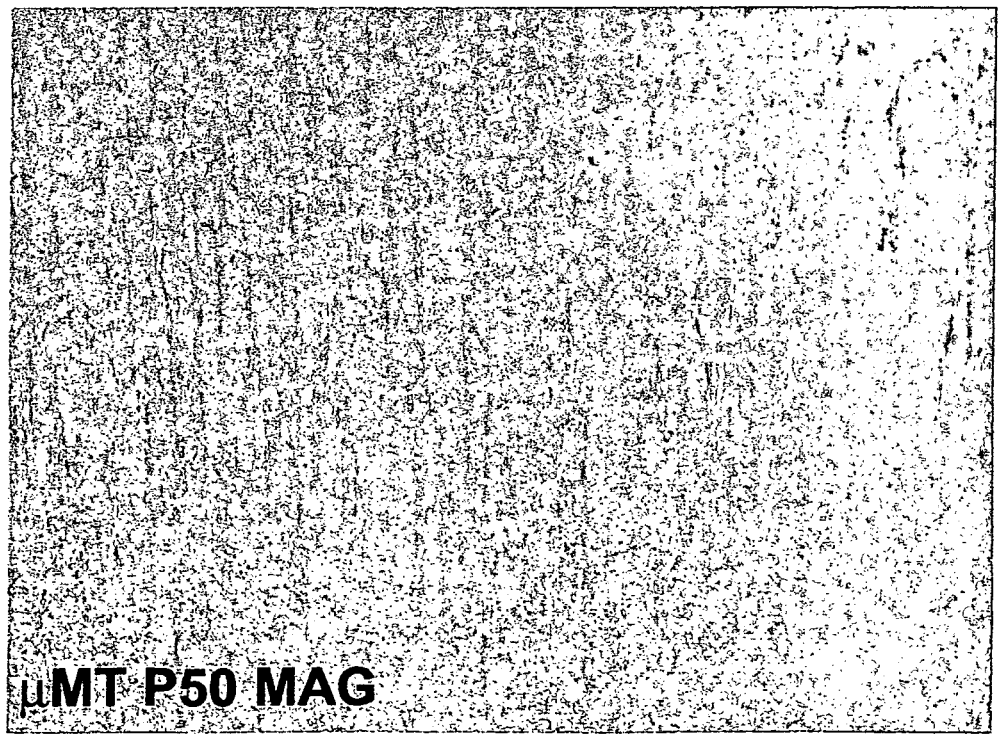

MEDICINAL COMPOSITIONS CONTAINING FC RECEPTOR γ CHAIN ACTIVATOR

TECHNICAL FIELD

The present invention relates to pharmaceutical compositions comprising a ligand for the γ chain of Fc receptors (FcRγ); agents for stimulating myelinogenesis; agents for stimulating the differentiation of oligodendroglial precursor cells, agents for activating Fyn tyrosine Kinase; agents for stimulating the expression of myelin basic protein; a method of detecting myelinogenetic oligodendroglias or precursor cells thereof; a method of examining FcRγ expression in animal tissues or cells; and reagent kits.

BACKGROUND ART

Myelin, a multi-layered membranous sheath enwrapping individual axons, is required for both the fast conduction of nerve impulses and for axonal function and integrity (1,2). Myelin is synthesized by oligodendroglia in the central nervous system (CNS) a process occurring shortly after the birth. Defects with myelin cause severe diseases in human; multiple sclerosis (MS) is one of such diseases, characterized by severe loss of myelin in the CNS. Although the disease was first described more than a century ago, both the etiology and cure remain largely unknown and uninvestigated (3). Only recently, a population of oligodendroglial precursor cells was first observed in MS lesions (4). Unraveling mechanisms that enable those endogenous precursor cells to be differentiated and/or strengthened so as to regenerate the lost myelin would prove to be an efficient therapeutic target. Therefore, comprehensive studies for elucidating the mechanism of myelinogenesis are of great importance in the treatment and cure of demyelinating diseases.

Myelin is composed of a limited number of myelin proteins. Myelin basic protein (MBP) comprises 30-40% of all myelin proteins within the CNS. MBP is indispensable in myelinogenesis, playing a crucial role in the compaction of the myelin sheath (5). MBP as regulates the expression of other myelin proteins such as myelin-associated glycoprotein (MAG), indicating that MBP is extremely important for myelinogenesis (6). The spontaneous Shiverer mouse, which has a natural knock-out of the MBP gene (7), exhibits severe hypomyelination of CNS axons, leading to premature death within 3 months. Specific isoforms of MBP containing exon 2 of the MBP gene play a regulatory role in myelinogenesis (8), suggesting that the preliminary events of myelinogenesis require MBP.

In the process of myelinogenesis, Fyn tyrosine kinase (Fyn) functions as an essential signaling molecule within oligodendroglia (9), stimulating the expression of MBP (10). Mice deficient in Fyn suffer severe decreases in MBP production, resulting in severe dysmyelination (9-11). Fyn, a non-receptor type tyrosine kinase, requires coupling to an adapter molecule in order to receive extracellular signals. Although myelin-associated glycoprotein (MAG) has been proposed as a candidate molecule responsible for the initial triggering of Fyn signals in myelination (9-13), MAG-deficient mice demonstrated only subtle myelin abnormalities (14,15). No significant differences in MBP expression were observed in MAG-deficient mice (14-16), casting doubt on the validity of MAG as the upstream signaling molecule which links extracellular signals to Fyn. Several researchers postulated that compensatory molecules may function in MAG-deficient mice; such molecules, however, have yet to be identified (17,18).

It was suggested that MAG is not the trigger of myelinogenesis but that hitherto unknown molecules are responsible for triggering (6). In addition, in vitro studies have revealed that the activation of Fyn during the morphological differentiation of oligodendroglia occurs prior to the first expression of MAG (19). It is MBP that regulates the expression of MAG in vivo (6).

It is an object of the present invention to identify the trigger that functionally couples to Fyn to cause the initial expression of MBP, thereby obtaining therapeutic strategies for diseases that result from defects with myelinogenesis. This molecule, i.e. the true trigger of myelinogenesis, must be expressed prior to the expression of MAG (i.e. early in the second week after birth; 6,20). Elucidation of this signal cascade will allow close understanding of the mechanism underlying myelinogenesis.

DISCLOSURE OF THE INVENTION

The present inventors have demonstrated that the γ subunit of the immunoglobulin Fc receptor (FcRγ), an essential signaling molecule in the immune system (reviewed in 21), is involved in myelinogenesis. FcRγ, which couples to Fyn (21), governs the initial expression of MBP in oligodendroglia. The present inventors propose that this FcRγ-Fyn-MBP cascade is essential in myelinogenesis. The present inventors detected Fc receptors, specific for immunoglobulin G, in oligodendroglia, suggesting that antibody-Fc receptor interactions may regulate myelinogenesis. CD45, an Fyn regulating molecule (22), co-expresses with FcRγ in oligodendroglia during myelinogenesis. The involvement of this signaling molecule in the process of myelinogenesis is supported by the discovery of a mutation in CD45 within some populations of patients with MS (23). The findings of the present inventors introduce a connection between the brain and the immune system, clarifying the mechanism of myelinogenesis. Elucidation of this correlation has provided future therapeutic strategies for demyelinating diseases/dysmyelinating diseases including MS. The present invention has been achieved based on these findings.

The present invention can be summarized as follows.
(1) A pharmaceutical composition comprising, as an active ingredient, a substance capable of activating FcRγ provided that the substance is not an immunoglobulin for intravenous injection.
(2) The pharmaceutical composition of (1) above, wherein the substance capable of activating FcRγ is a ligand for FcRγ, the ligand produced at least one effect selected from the following (A), (B) and (C):
(A) stimulating the differentiation of oligodendroglial precursor cells;
(B) activating Fyn tyrosine kinase;
(C) stimulating the expression of myelin basic protein.
(3) The pharmaceutical composition of (2) above, wherein the ligand for FcRγ is an anti-FcRγ antibody.
(4) The pharmaceutical composition of (1) above, wherein the substance capable of activating FcRγ is a ligand for any one of Fc receptors capable of coupling to FcRγ, the ligand producing at least one effect selected from the following (a), (b) and (c);
(a) stimulating the differentiation of oligodendroglial precursor cells;
(b) activating Fyn tyrosine kinase;
(c) stimulating the expression of myelin basic protein.
(5) The pharmaceutical position of (4) above, wherein the ligand for any one of Fc receptors capable of coupling to FcRγ is a ligand for type I Fcγ receptor (FcγRI).

(6) The pharmaceutical composition of (5) above, wherein the ligand for FcγRI is an anti-FcγRI antibody.

(7) The pharmaceutical composition of (4) above, wherein the ligand for any one of Fc receptors capable of coupling to FcRγ is a ligand for type III Fcγ receptor (FcγRIII).

(8) The pharmaceutical composition of (7) above, wherein the ligand for FcγRIII is an anti-FcγRIII antibody (9) The pharmaceutical composition of (1) above, wherein the substance capable of activating FcRγ is a subclass of IgG having a high binding property to FcγRI.

(10) The pharmaceutical composition of (9) above, wherein the subclass of IgG is IgG3.

(11) The pharmaceutical composition of (1) above, wherein the substance capable of activating FcRγ is IgG2b.

(12) The pharmaceutical composition of any one of (1) to (11) above, wherein the composition is for stimulating the differentiation of oligodendroglial precursor cells.

(13) The pharmaceutical composition of ant one of (1) to (12) above, wherein the composition is for activating Fyn tyrosine kinase.

(14) The pharmaceutical composition of any one of (1) to (13) above, wherein the composition is for stimulating the expression of myelin basic proteins.

(15) The pharmaceutical composition of any one of (1) to (14) above, wherein the composition is for stimulating myelinogenesis.

(16) The pharmaceutical composition of any one of (1) to (15) above, wherein the composition is for preventing and/or treating at least one disease selected from the group consisting of demyelinating diseases, dysmyelinating diseases and myelinoclasis.

(17) An agent for stimulating myelinogenesis comprising, as an active ingredient, a substance capable of activating FcRγ, provided that the substance is not an immunoglobulin for intravenous injection.

(18) An agent for stimulating the differentiation of oligodendroglial precursor cells comprising, as an active ingredient, a substance capable of activating FcRγ.

(19) An agent for stimulating Fyn tyrosine kinase comprising, as an active ingredient, a substance capable of activating FcRγ.

(20) An agent for stimulating the expression of myelin basic protein comprising, as an active ingredient, a substance capable of activating FcRγ.

(21) A method of detecting myelinogenetic oligodendroglias or precursor cells thereof comprising using the expression of FcRγ in oligodendroglias or precursor cells thereof as an indicator.

(22) The method of (21) above, further comprising using as another indicator the expression of at least one marker selected from the group consisting of PDGFαR, MAG, A2B5, 04, 01, MBP, PLP, DM-20, CNPase, MOG, NG2 and AN2 in oligodendroglias or precursor cells thereof.

(23) A method of examining FcRγ expression in animal brain tissues or cells by immunohistochemical or immunocytochemical analysis.

(24) The method of (23) above, further comprising examining the expression of at least one marker selected from the group consisting of PDGFαR, MAG, A2B5, 04, 01, MBP, PLP, DM-20, CNPase, MOG, NG2 and AN2 in oligodendroglias or precursor cells thereof.

(25) A method of examining FcRγ expression in animal brain tissues or cells by a gene amplification method.

(26) A method of examining FcRγ expression in animal brain tissues or cells by Western blotting.

(27) The method of (26) above, further comprising examining the expression of at least one marker selected from the group consisting of PDGFαR, MAG, A2B5, 04, 01, MBP, PLP, DM-20, CNPase, MOG, and AN2 in oligodendroglias or precursor cells thereof.

(28) An immunohistological or cell-staining reagent kit comprising an anti-FcRγ antibody.

(29) The kit of (28) above, further comprising at least one antibody selected from the group consisting of anti-PDGFαR antibody, anti-MAG antibody, A2B5 antibody, 04 antibody, 01 antibody, anti-MBP antibody, anti-PLP antibody, anti-DM-20 antibody, anti-CNPase antibody, anti-MOG antibody, NG2 antibody and AN2 antibody.

(30) A Western blotting reagent kit comprising an anti-FcRγ antibody.

(31) The kit of (30) above, further comprising at least one antibody selected from the group consisting of anti-PDGFαR antibody, anti-MAG antibody, A2B5 antibody, 04 antibody, 01 antibody, anti-MBP antibody, anti-PLP antibody, anti-DM-20 antibody, anti-CNPase antibody, anti-MOG antibody, NG2 antibody and AN2 antibody.

(32) A gene amplification reagent kit comprising at least one pair of primers capable of specifically amplifying the mRNA of FcRγ.

The term "activating FcRγ" used herein triggering or enhancing an FcRγ-dependent intracellular cascade. As a specific example of the FcRγ-dependent intracellular cascade, FcRγ-Fyn-MBP cascade may be given. It has been demonstrated by the present inventors that in this FcRγ-Fyn-MBP cascade, FcRγ couples to Fyn, regulating the initial expression of MBP in oligodendroglia.

It is possible to activate FcRγ, for example, cross-linking FcRγ with an antibody. Alternatively, it is possible to activate FcRγ by cross-linking type I Fc receptor γ (hereinafter referred to as "FcγRI") or type III Fc receptor γ (hereinafter referred to as "FcγRIII") (Fc receptors for IgG) to which FcRγ is coupled to, with an antibody to FcγRI or FcγRIII. It was also been reported that FcRγ is activated when FcεRI is cross-linked with an antibody to FcεRI (reviewed in H. Turner & J. P. Kinet, Nature 402, B24 (1999); see also the references cited in this review). In the cross-linking of FcεRI, it has been reported that calcium signals by IP3R as well as ERK and JNK are regulated through complicated Coupling of Lyn, Syk, PLCγ, etc. (reviewed in H. Turner & J. P. Kinet, Nature 402, B24 (1999); see also the references cited in this review; for FcγRs, see J. V. Ravetch & S. Bolland, Ann. Rev. Immunol. 19:275 (2001) and the references cited therein). Whether it is downstream of FcεRI or FcγRs, the cascade is considered to be entirely FcRγ-dependent. Nevertheless, FcRγ seems to have cascades in a cell-specific manner.

The term "immunoglobulin for intravenous injection" used herein means an immunoglobulin extracted from a pool of many and unspecified imunoglobulins. Such immunoglobulin is polyclonal, and its major component is IgG. Such immunoglobulin is used as medical IVIg.

The term "ligand for the γ chain of Fc receptors" (hereinafter referred to as the "ligand for FcRγ") means a substance which specifically binds to the γ chain of Fc receptors (hereinafter referred to as "FcRγ").

The term "stimulating the differentiation of basic protein" used herein refers to inducing any of the morphological/chemical changes observed during the period up to the maturation of oligodendroglial precursor cells into oligodendroglia. Specific examples of such changes include the appearance of processes from oligodendroglial precursor cells, or increase in the expression levels of proteins such as MBP that are indispensable for myelinogenesis.

The term "activating Fyn tyrosine kinase" used herein refers to producing one or both of the following effects:

increasing the enzyme activity of Fyn tyrosine kinase (qualitative increase) or increasing the expression level of Fyn itself (mRNA or protein) (quantitative increase). It is speculated that the qualitative increase requires CD45.

The term "stimulating the expression of basic protein" used herein refers to causing or increasing the expression of myelin basic protein; the expression of myelin basic protein may be either at the RNA level or at the protein level.

As myelin basic protein (hereinafter, referred to as "MBP"), isoforms of 14.0, 17.0, 18.5 and 21.5 kD are known. These isoforms are generated by selective use of the seven exons on the MBP gene. Isoforms whose expression is promoted by a ligand for FcRγ are mainly those isoforms which comprise exon 2 (i.e. isoforms of 17.0 and 21.5 kD).

The term "being coupled to FcRγ" used herein refers to Co.-operating with FcRγ functionally or physically. For example, FcγRI contains FcRγ as a constituent molecule (physical co-operation), and the FcγRI signaling cascade is FcRγ-dependent (functional co-operation).

The term "stimulating myelinogenesis" used herein means: replacing or repairing removed myelin sheaths in demyelinating diseases; completing or repairing by replacement those myelin sheaths which were formed incompletely in dysmyelinating diseases; and stimulating foreign oligodendroglias or oligodendroglial precursor cells introduced into a patient's body so that they actually form myelin sheaths in the body to thereby enhance their forming ability in transplantation/regeneration medicine.

The term "demyelinating diseases" used herein refers to those diseases wherein myelin sheaths once formed are denatured or removed for some reason; the term "dysmyelinating disease" used herein refers to those diseases wherein myelinogenesis itself is impaired for some reason; the term "transplantation/regeneration medicine" used herein refers to medicine wherein an oligodendroglia prepared by some method is transplanted into patients to thereby replace and repair impaired myelin sheaths or allow formation of myelin sheaths in the patients in order that low or no myelinogenesis is artificially compensated.

Examples of "demyelinating diseases" include, but are not limited to, multiple sclerosis, optical neuromyelitis, and acute diffuse encephalomyelitis. Examples of "dysmyelinating diseases" include, but are not limited to, Krabbe's disease, metachromatic leukodystrophy and adrenoleukodystrophy. Other diseases where dysmyelination is caused by metabolic disorders are often classified into metabolic diseases in spite of their being dysmyelinating diseases. However, all diseases where myelinogenesis is impaired can be defined as dysmyelinating diseases.

The term "myelinoclasis" used herein refers to physical disintegration for some reason of myelin sheaths, once formed or being formed, and the resultant deprivation of their function. For example, in encephalomyelitis and the like, immune cells generally destroy myelin sheaths in an inflammatory manner.

In the method of the invention for detecting myelinogenetic oligodendroglias or precursor cells thereof, the expression of FcRγ in oligodendroglias or precursor cells thereof is used as an indicator. The expression of FcRγ may be either at the RNA level or at the protein level.

The term "marker" used herein means a substance which may serve as an indicator when the identity of a specific tissue or cell is examined (e.g. FcRγ) or a substance which is useful in searching for the indicator (e.g. anti-FcRγ antibody).

The term "immunohistochemical or immunocytochemical analysis" used herein refers to a means of detecting a specific antigen present in a tissue or cells by an antigen-antibody reaction. For example, a specific antigen present in a tissue or cells may be visualized with a labeled antibody and then observed under a microscope (direct method). Alternatively, a method may be employed in which a primary antibody specific to the antigen and a labeled secondary antibody specific to the primary antibody are used (indirect method). It is also possible to detect the fluorescence of a labeled secondary antibody by flow cytometry (FACS).

The term "gene amplification method" used herein means a method of amplifying DNA in chain reactions using DNA polymerase.

The term "western blotting" used herein means a method in which a protein of interest separated by electrophoresis is transferred onto a nitrocellulose membrane, PVDF membrane or the like and then detected with an antibody.

In one embodiment of the present invention, a pharmaceutical composition comprising as an active ingredient a substance capable of activating FcRγ may be used to prevent and/or treat at least one disease selected from the group consisting of demyelinating diseases, dysmyelinating diseases and myelinoclasis. In the future, a therapeutic treatment in which neural stem cells, ES cells or subject-derived oligodendroglias are transplanted and regenerated will be practiced. (Experiments to transplant Schwann cells, which form myelin in the peripheral nerve system, into the central system have already begun on human subjects in Yale University.) When such a treatment has become possible, the technique of the present invention will be applicable as a booster for myelin formation. In myelinoclasis occur secondary (e.g. destruction of nerve axons precedes destruction of myelin sheaths), if an attempt to artificially repair the destructed nerve axons has become possible, oligodendroglial transplantation and myelin regeneration will similarly become necessary. The technique of the present invention will also be applicable to such a case.

In another embodiment of the present invention it is possible to use FcRγ as a marker for oligodendroglias or precursor cells thereof. FcRγ-positive oligodendroglias may be regarded as cells having the potential for myelinogenesis.

The present specification encompasses the contents of the specification and/or drawings of Japanese Patent Application No. 2001-229553 based on which the present patent application claims priority.

BRIEF DESCRIPTION OF THE DRAWINGS

FIG. 1 shows FcRγ expressions in oligodendroglial precursor cells (OPC) and immature oligodendroglia in vitro. A: RT-PCR analysis of FcRγ expression. OPC express FcRγ (a) but not CD3ζ (b). Bone marrow-derived mast cells and splenocytes (58) were used as positive controls. Semi-quantitative RT-PCR revealed approximately equal expression levels of FcRγ mRNA in immature oligodendroglia and in mast cells (data not shown). B: Immunocytochemical analysis of FcRγ expression. FcRγ is expressed in A2B5-positive oligodendroglial precursor cells (a, b), O4-positive (c, d), and O1-positive immature oligodendroglias (e, f). Bar: 15 μm. C: Western blotting analysis of FcRγ revealed significant expression in immature oligodendroglia (37) derived from wild type mice (Wt), but not in immature oligodendroglia from FcRγ-deficient mice (FcRγ−/−) (58).

FIG. 2 shows distribution of FcRγ-expressing cells in vivo. Coronal sections of the cerebrum indicate that FcRγ-expressing cells are distributed mainly in the SVZ at P0 (a). These cells expand into the white matter at P4 (b), localizing mainly within the white matter at P7 (c). FcRγ-positive cells are observed in the SVZ (subventricular zone), adjacent to the mouse-Musashi-1 (m-Msi-1)-positive cell layer in the VZ (ventricular zone) (41), suggesting that FcRγ-positive calls are derived from neural stem cells (d, e). FcRγ-positive cells are maintained in the adult CNS with a distribution similar to that at P7; the population is localized in the supraventricular area of the white matter and occurs, rarely within the gray matter (f). LV: lateral ventricle, cc: corpus callosum, vz: ventricular zone, svz: subventricular zone, CTX: cerebral cortex, CG: cingulum, CPu: caudate putamen. Bar: 50 µm (c), 25 µm (e), 50 µm (f).

FIG. 10(a-d), which resembles FIG. 9, shows staining of MAG. Legends are the same as in FIG. 9. Panel e shows the brain of MBP-deficient Shiverer mouse (MBP-/-). The present inventors put forth a cascade model of FcRγ→Fyn→MBP. As shown in Panel d in FIG. 9. MBP is hardly detected when both FcRγ and Fyn are knocked out. Hence, the inventors examined whether the phenotype of the animal that lacking MBP from the beginning would be similar to the phenotye of the double-deficient animal. As it turned out, the MAG expression patterns of MBP deficient mice and Fyn/FcRγ double-deficient mice (FcRγ-/-Fyn-/-) were similar to each other. As shown in the graph in Panel f, they also have similar numbers of MAG-positive immature oligodendroglias. These results demonstrated that FcRγ and Fyn are essential for the expression of MBP.

FIG. 11(a-d) shows the cerebral cortex of mice of the indicated genotypes 1.5 months after birth (P1.5M). MBP is stained. Fyn- or FcRγ-deficient mice show (i) slightly thin cerebral cortex and (ii) weak MBP staining. Further Fyn/FcRγ double-deficient mice show (i) extremely thin cerebral cortex and (ii) substantial fading away of MBP staining. These results suggest that the phenomena at day 10 after birth shown in FIGS. 9 and 10 are not compensated during aging, but remain as a permanent defect. Panels e to h show Nissl staining of mice with the genotypes and ages indicated below individual images. The arrow shows the occurrence of hydrocephalus. The arrow points an area Corresponding to the ventricle where accumulation of excessive cerebrospinal fluid is observed. Similar hydrocephalus is observed at P10 though not so severe as at P1.5M.

FIG. 12(a, b) shows images of cultured OPCs. Panel a is a phase-contrast image. Panel b shows immunological staining of CD45. Arrows indicate CD45-positive OPCs. On the other hand, arrowheads indicate less stained (rather negative) OPC. Positive cells represent OPCs that have more distinct processes and are more differentiated. Negative cells represent OPCs that are differentiated only slightly. These results suggest that CD45 is expressed in a differentiation-associated manner. Panel c is an image of the brain from a wild-type mouse 7 days after birth showing an area around the endocyst. MAG-stained oligodendroglias also show CD45-staining (arrows). This indicates that the oligodendroglia is CD45-positive. On the other hand, arrowheads point to those cells which are positive to CD45 alone. These may be cells other than oligodendroglial cells, or they may be undifferenciated oligodendroglia that are yet to express MAG. "Fim" represent the fimbria, and "L" represents the lateral ventricle. Panel d and e show CD45 staining. These images were taken in order to examine whether the CD45 antibody used is reacting specifically. In wild-type mice, CD45-positive cells are stained in the white matter, particularly in CC (corpus callosum). In CD45-deficient nice (CD45-/-), no such staining is observed, suggesting that the antibody is reacting specifically. However, even in CD45-deficient mice, the structure called choroids plexus located in the LV (lateral ventricle) is stained with CD45. This site is known as a place where non-specific reaction occurs. CTX: cerebral cortex, CC: corpus callosum, SVZ: subventricular zone.

FIG. 13a shows images of cultured OPCs from wild-type mouse and CD45-deficient mouse (CD45-/-) without stimulation (control) or with 24-hr stimulation using anti-FcRγ antibody. While the wild-type cells display morphological differentiation upon stimulation, CD45-deficient cells do not. These results show that CD45 is necessary for the differentiation of OPC. Panel b shows the results of western blotting of the cells shown in Panel a. This time, cells were stimulated not only with FcRγ but also with IgG. When stimulated with IgG and FcRγ, wild-type OPC displayed increased MBP expression, but CD45-deficient mouse did not show such increase. These results show that CD45 is necessary for the differentiation of OPC. Panel co shows detection by Western blotting of MBP in myelin fractions extracted from brains of wild-type mouse, CD45-deficient mouse and Fyn-deficient mouse (Fyn-/-) at P10. As seen from this image, CD45-deficient mouse and Fyn-deficient mouse show reduced MBP, as compared to the wild-type mouse. This supports the results of analysis of the tissues (d-h), and also suggests that both CD45 and Fyn are important for myelinogenesis (MBP expression). Panels d and e show myelin in the striatum of wild-type mouse and CD45-deficient mouse at day 10 after birth by immunohistochemical staining of MBP. "LV" represents the lateral ventricle. CD45-deficient mouse shows decreased expression of MBP. Panels f, g and h show immunohistological staining of MAG at P10. Since CD45 is speculated to be responsible for the activation of Fyn, comparison is made with Fyn-deficient mouse. The wild-type mouse shows a great number of MAG-positive oligodendroglias in the corpus callosum (CC) and cerebral cortex (CTX), whereas CD45-deficient and Fyn-deficient mice show decrease of MAG-positive cells to similar extents. These results support that CD45 is involved in the activation of Fyn.

FIG. 14 shows observation of myelin in the striatum of wild-type mouse and CD45-deficient mouse (CD45-/-) at 1.5 months after birth. Immunohistological staining of MBP shows myelin stained in an uneven, spotted manner in CD45-deficient mouse, suggesting disintegration of myelin (or dysmyelination from the beginning). This means that the myelin abnormality in FIGS. 12 and 13 still remains at 1.5 months after birth and is not compensated. (The image at P10 is not merely a growth defect.)

FIG. 15 shows immunohistochemical staining of MAG in IgG deficient µMT mouse and wild-type mouse at P7. The images show coronal sections of the cerebrum. The µMT mouse shows reduced myelin, suggesting that IgG is ally required in myelinogenesis as a physiological function.

FIG. 16 shows immunohistochemical staining of MAG in IgG-deficient μMT mouse and wild-type mouse at P10. The images show coronal sections of the cerebrum. The μMT mouse shows reduced myelin, suggesting that IgG is actually required in myelinogenesis as a physiological function.

FIG. 17 shows immunohistochemical staining of MAG in IgG-deficient μMT mouse and wild-type mouse (Wt) at P50 (adult). The images show inside of the cerebrum. The μMT mouse shows reduced myelin, suggesting the IgG is actually required in myelinogenesis as a physiological function.

BEST MODE FOR CARRYING OUT THE INVENTION

Figure 3:
FIG. 3 shows that FcRγ-positive cells are derived from the oligodendroglial lineage in vivo. A: Double-labeling of coronal sections of the cerebrum at P0 demonstrates that FcRγ-positive cells are distributed mainly in the SVZ (a). The majority of these cells do not co-localize with GFAP-expressing cells, i.e. the astroglial lineage cells (b). The distribution of Ox-42-positive cells of the microglial lineage is distinct from that of the FcRγ-positive cells (c). Therefore, FcRγ-positive cells at the age of interest are predominantly derived from the oligodendroglial lineage. Panel b is a higher magnification of Panel a (shown in box). o: oligodendroglial cells, a: astroglial cells, m: microglial cells. Bar: 50 µm (a, c), 25 µm (b). B: Double-labeling images of coronal sections of the cerebrum at P7 are take from the pre-myelinated corpus callosum. FcRγ and Fyn co-localize at the cell-membrane (arrowheads; a) MAG co-labels FcRγ-positive oligodendroglia (arrowheads); the expression, however, is stronger at the tips of the cellular processes (b). Bar; 25 µm. C: Identity of FcRγ-positive cells within the adult CNS. FcRγ-MBP-double positive oligodendroglial cells are observed within the white matter, providing a similar pattern to the one seen in the neonatal CNS (a). In contrast, a small subpopulation of GFAP-positive cells, found predominantly within the adult SVZ, is also FcRγ-positive (b). Bar: 25 µm. D: Analysis of serial sections revealed similar patterns (arrows and arrowheads) for FcRγ (a), Fyn (b) and MBP (c). Images obtained from the corpus callosum and from a part of the fornix at P7 indicate those patterns. Unlikely Fyn and MBP, FcRγ is also expresses within axons (46). Bar: 50 µm.

Hereinbelow, the present invention will be described in more detail.

The pharmaceutical compositions of the invention comprise, as an active ingredient, a substance capable of activating FcRγ. Specific examples of the substance capable of activating FcRγ include ligands for FcRγ that produce at least one effect selected from the following (A), (B) and (C):
(A) stimulating the differentiation of oligodendroglial precursor cells;
(B) activating Fyn tyrosine kinase;
(C) stimulating the expression of myelin basic protein.
Alternatively, the substance need not produce any of the effects (A), (B) and (C) above as along as it specifically couples to FcRγ and stimulates myelinogenesis. Specific examples of ligands for FcRγ include, but are not limited to, anti-FcRγ antibodies. Anti-FcRγ antibodies include polyclonal antibodies and monoclonal antibodies.

Anti-FcRγ antibodies may be prepared by conventional methods.

For example, in order to prepare polyclonal antibodies, animals are immunized with FcRγ, the immunogen. Then, an anti-FcRγ antibody-containing material is collected from the animal, and the antibody of interest is separated and purified therefrom. Alternatively, a partial peptide of FcRγ may be used. It is also possible to immunize animals with an artificial peptide synthesized based on the nucleotide sequence encoding FcRγ (GenBank M33195 (human FcRγ)). If a short peptide (generally, 6-18 amino acids in length) is used as an immunogen in such a case, the peptide may be conjugated with a carrier protein such as keyhole limpet hemocyanin. When the FcRγ protein is administered for immunization, usually 50-100 μg is used.

In order to prepare monoclonal antibodies, animals with high antibody titers are selected from the above-described immunized animals, and the spleen or lymph nodes are removed from them 3 to 5 days after the final immunization. Antibody-producing cells contained therein are fused to myeloma cells, followed by selection of hybridomas capable of stable production of high-titer antibodies. The hybridoma is grown in the abdomen of animals. Then, the monoclonal antibody of interest may be purified from the abdominal dropsy or may be purified from the serum or the like of the animal. Alternatively, the hybridoma way be cultured in a medium to allow antibody production, and then the monoclonal antibody may be purified from the culture supernatant or the like. Methods of preparing monoclonal antibodies are described in P. N. Nelson et al., J. Clin. Pathol.: Mol. Pathol. 53, 111-117 (2000), which is cited herein by reference.

Methods of preparing FcRγ, the immunogen, are described in Takai et al. (58) and the references cited therein, which are cited herein by reference. With respect to human FcRγ, it is easy to prepare a synthetic peptide based on the published sequence for human FcRγ (GenBank M33195).

For the immunization of animals (e.g. mammals), the immunogen FcRγ is administered alone or with a diluent, carrier, etc. to a site capable of antibody production. Preferably, the immunogen is administered by subcutaneous injection. At this time, complete or incomplete Freund's adjuvant may also be administered in order to enhance antibody productivity. Usually, the administration of the immunogen is performed once a week; for monoclonal antibodies, the administration may be performed once or twice a week, and for polyclonal antibodies, the administration may be performed 3 or 4 times a week.

Specific examples of animals to be immunized include, but are not limited to, monkey, rabbit, dog, guinea pig, mouse, rat, sheep, goat and chicken.

Antibodies are recovered from the blood, abdominal dropsy, etc. of the thus immunized animals. The most common method used for measuring antibody titers is ELISA (Enzyme Linked Immunosorbent Assay). For further examination, immunohistochemical and Western blotting may be used. For details, see Nelson et al., J. Clin. Pathol.: Mol. Pathol. 53, 113-117 (2000).

The separation and purification of antibodies may be performed according to conventional methods for separation/purification of immunoglobulin (e.g. salting out, alcohol precipitation, isoelectric precipitation, electrophoresis, absorption & description with ion exchanges (such as DEAE), ultracentrifugation, gel filtration, specific purification methods in which a specific antibody is recovered with an antibody-binding material or an active adsorbent such as protein-A and then the binding is dissociated to thereby obtain the antibody).

The thus prepared antibody contains IgG as a major component with minor amounts of other imunoglobulins such as IgM, IgA, etc. This antibody binds to FcRγ specifically.

Anti-FcRγ antibody-producing hybridomas may be prepared by immunizing animals (e.g. mouse) in the same manner as described for polyclonal antibody preparation, selecting those individuals exhibiting high antibody titers from the immunized animals removing the spleen or lymph nodes from them within one week after the final immunization, and then fusing antibody-producing cells contained therein with myeloma cells. Cell fusion procedures may be performed according to known methods, e.g. the method of Koehler and Milstein (Nature, 256, 495, (1975)). Examples of useful fusion promoters include polyethylene glycol (PEG), Sendai virus, etc. Preferably, PEG is used. Examples of myeloma cells useful in the invention include Sp2/0, NS1, NS0, X63Ag8, etc. Preferably, Sp2 is used. A preferable ratio of the number of antibody-producing cells used (spleen cells) to the number of myeloma cells is from about 1:1 to about 1:2. When PEG (preferably, PEG1000 to PEG6000) is added at a concentration of about 50% and the resultant cell mixture is incubated at 37° C. for about 20-30 minutes, an efficient cell fusion can be achieved.

Separation and purification of the anti-FcRγ monoclonal antibody may be performed in the same manner as described for the polyclonal antibody, according to conventional methods for separation and purification of imunoglobulins.

As long as the anti-FcRγ antibody binds to FcRγ specifically and produces a desired effect, it may be an antibody of any class of IgG, IgA or IgM, or it may be their Fab' or Fab fraction that is left after removal of Fc or Fc region, or a polymer thereof. Alternatively, a chimeric antibody may be used which is obtained by fusing the variable gene moiety of anti-FcRγ antibody to the human immunoglobulin constant gene and expressing the resultant gene as a recombinant.

The anti-FcRγ antibody may be modified with sugar chains which would be disrupted by enzymes present in the brain.

Examples of the substance capable of activating FcRγ other than anti-FcRγ include, but are not limited to, the following.
1) anti-FcγRI antibodies
2) anti-FcγRIII antibodies
3) antagonists to FcγRII
4) artificial compounds that are presumed to have the ability to bind to FcRγ in view of the structure of FcRγ
5) subclasses of IgG having a high binding property to FcγRI among IgG
6) anti-FcεRI antibodies The anti-FcγRI antibody in 1) and the anti-FcγRIII antibody in 2) may be prepared based on the above-described preparation method for anti-FcRγ antibody, using FcγRI and FcγRIII, respectively, as an immunogen.

The antagonist to FcγRII in 3) may be any substance which has an effect of inhibiting a function that acts on FcRγ inhibitorily (i.e. negatively).

Since FcγRII (type II Fc receptor) acts inhibitorily upon the activity of FcRγ, it is believed that stimulation of FcRγ would produce more effect if FcγRII is blocked with an antagonist in advance.

The artificial compound that is presumed to have the ability to bind to FcRγ in view of the structure of FcRγ mentioned in 4) may be any Compound as long as it is capable of activating FcRγ. The ability to bind to FcRγ may be estimated by IP-Western blotting or the like. For example, the compound may be reacted with oligodendroglia, followed by immunoprecipitation (IP) with anti-FcRγ antibody. If the recovered substance is the artificial compound, the compound is estimated to have the ability to bind to FcRγ. The artificial compound thus estimated to have the binding ability may be a commercial product or may be synthesized chemically.

As subclasses of IgG a high binding property to FcγRI a IgG, there may be enumerated IgG3, IgG1, IgG4, IgG2, etc. for human and IgG2, IgG1, IgG2b, IgG3, etc. for mouse. FcγRI is a high-affinity IgG receptor, and FcγRIII a low-affinity IgG receptor. For the activation of FcγRI, an IgG subclass with a high binding ability to FcγRI (e.g. IgG3 for human) may be administered selectively. For a relevant review,. J. E. Gessner et al., Ann. Hematol. 76:231-248 (1988). These IgG subclasses may be prepared by mixing the IgGs obtained from subclass-specified hybridomas to make them polyclonal, or by obtaining an antibody to a non-reactive hybridoma.

The anti-FcεRI antibody of 6) above may be prepared based on the above-described preparation method for anti-FcRγ antibody, using FcεRI as an immunogen.

The above-describes substances capable of activating FcRγ may be used independently or in combination.

The substance capable of activating FcRγ may be administered either alone or as a pharmaceutical composition comprising pharmaceutically acceptable carriers, diluents or excipients, to mammals (e.g. human, rabbit, dog, cat, rat, mouse) orally or parenterally. Dose levels may vary depending upon the subject to be treated, target disease, symptom, administration route, and so on. When used for preventing or treating adult patients with demyelinating diseases (e.g. multiple sclerosis), a substance capable of activating FcRγ (e.g. anti-FcRγ antibody) is usually administered at about 150-500 mg/kg body weight, preferably about 400-500 mg/kg body weight per dose, about once or twice a month. Preferably, the above-mentioned dose is administered by intravenous injection continuously for 2-3 days at the beginning of the treatment. For other parenteral administration routes and oral administration route, similar doses may be administered. When the condition of the patient is particularly severe, the dose may be increased.

As compositions for oral administration, solid or liquid preparations may be used. More specifically, tablets (including sugar-coated, tablets and film-coated tablets), pills, granules, powder, capsules (including soft capsules), syrups, emulsions, suspensions, or the like may be enumerated. These preparations may be formulated by conventional methods and may contain carriers, diluents or excipients conventionally used in the field of pharmaceutical manugacturing. For example, carriers and excipients for tablets include lactose, starch, sucrose, magnesium stearate, etc.

As compositions for parenteral administration, injections and suppositories may be mentioned, for example. Injections may be in such forms as intravenous injections, subcutaneous injection, intradermal injection, intramuscular injection, and drip injection. Such injections may be formulated by conventional methods. Specifically, they are prepared by dissolving, suspending or emulsifying a substance capable of activating FcRγ in an aseptic aqueous or oily liquid. Examples of aqueous liquids for preparing injections include physiological saline and isotonic solutions containing glucose and other auxiliary agents. These aqueous liquids may be used in combination with appropriate auxiliary solubilizers such as alcohol (e.g. ethanol), polyalcohol (e.g. propylene glycol, polyethylene glycol), or nonionic surfactant (e.g. Polysorbate 80, HOO-50 (polyoxyethylene (50 mol) adduct of hydrogenated castor oil)). Examples of oily liquids for injection include sesame oil, soybean oil, etc. They may be used in combination with an auxiliary solubilizer such as benzyl benzoate, benzyl alcohol, etc. Usually, the prepared injections are filled in appropriate ampoules. Suppositories for rectal administration may be prepared by mixing a substance capable of activating FcRγ with a conventional suppository base.

The above-described pharmaceutical compositions for oral or parenteral administration may be prepare into unit dosage forms so that appropriate amounts of active ingredients are administered. Such unit dosage forms include tablets, pills, capsules, injections (ampoules), suppositories, etc.

The above-described pharmaceutical composition may contain other active ingredient unless undesirable interaction will emerge from formulation with the substance capable of activating FcRγ. For example, an antagonist to FcγRII may be administered in order to enhance the effect of the composition.

The substance capable of activating FcRγ is not only useful in such pharmaceutical compositions, but also useful in other applications. For example, the substance may be used as a reagent for experiments in order to stimulate myelinogenesis, stimulate the differentiation of oligodendroglial precursor cells, activate Fyn tyrosine kinase, or stimulate the expression of myelin basic protein; or the substance may be used as an additive for use in an artificial culture system for oligodendroglial precursor cells.

In the method of the invention of detecting myelinogenetic oligodendroglias or precursor cells thereof, FcRγ expression in oligodendroglias or precursor cells thereof is used as an indicator. The expression of FcRγ in oligodendroglial or precursor cells thereof nay be examined by the methods to be described later in Examples (e.g. immunohistochemical or immunocytochemical analysis, gene amplification methods, Western blotting, etc.). Further, the expression of at least one marker selected from the group consisting of PDGFαR, MAG, A2B5, 04, 01, MBP, PLP, DM-20, CNPase, MOG, NG2 and AN2 in oligodendroglias or precursor cells thereof may be used as another indicator. With the use of the expression of these markers as indicators, more accurate detection becomes possible. Among the above markers, 04, PDGFαR, NG2 and DM20 (which are markers for immature oligodendroglia) are preferably selected.

Hereinbelow, one example of procedures for examining FcRγ expression in animal brain tissues or cells by immunohistochemical or immunocytochemical analysis is described below.

When immunohistochemical analysis is used, brain tissues removed from animals are first fixed, and then paraffin sections are prepared. After deparaffination, a primary antibody is added to the section dropwise and reacted at an appropriate temperature for an appropriate period. After the primary reaction, the section is washed and then reacted with a secondary antibody at an appropriate temperature for an appropriate period. When a biotin-labeled antibody is used as the secondary antibody, the section is further reacted with HRP-labeled streptavidin at an appropriate temperature for an appropriate period. After washing, the section is stained with a solution containing DAB. It is preferable to perform counter staining with methyl green or the like.

When immunocytochemical analysis is used, fixed tissues can be reacted with a primary antibody without preparation of sections. Generally, when cells are to be examined, a secondary antibody is labeled with a fluorescent dye (such as FTTC) and the fluorescence is observed with a fluorescent microscope.

For details of procedures for the method of examining FcRγ expression in animal brain tissues or cell by immunohistochemical or immunocytochemical analysis, see Example described later.

Hereinbelow, one example of procedure for examining FcRγ expression in animal brain tissues or cells by a gene amplification method is described.

Total RNA is extracted from animal brain tissues or cells. The RNA is subjected to RT-PCR using an appropriate pair of primers to thereby detect mRNA of FcRγ. The appropriate pair of primers is so designed that a specific region of the nucleotide sequence of human FcRγ-mRNA (GenBank M33195), for example, can be amplified specifically. The specific region to be amplified is determined considering the following points:
1) to select a region where restriction enzymes can be used effectively;
2) to select a region with the highest possible C+G content.

In one Example described later, a pair of primers (SEQ ID Nos: 1 and 2) is designed by making predictions based on the mouse FcRγ-mRNA sequence of GenBank NM010185 (SEQ ID No: 17). The primer represented by SEQ ID NO: 1 is so designed that a sequence from positions 178 to 195 in the FcRγ-mRNA sequence shown as SEQ ID NO: 17 is recognized. The primer represented by SEQ ID NO: 2 is so designed that a sequence from positions 284 to 303 in the same FcRγ-mRNA sequence is recognized.

For details of procedures for the method of examining FcRγ expression in animal brain tissues or cells by a gene amplification method, see Examples described later.

Hereinbelow, one example of procedures for examining FcRγ expression in animal brain tissues or cells by Western blotting is described.

Protein sample solutions are prepared from animal brain tissues or cells and subjected to SDS-polyacrylamide gel electrophoresis (SDS-PAGE) The resultant SDS-PAGE gel is transferred onto a membrane and blocked. After washing, the membrane is reacted with a primary antibody and an enzyme-labeled secondary antibody in this order. After appropriate washing, a substrate for the enzyme is added for color formation.

For details of procedures for the method of examining FcRγ expression in animal brain tissues or cells by Western blotting, see Examples described later and C. Seiwa, I. Sugiyama, T. Yagi, T. Iguchi, H. Asoa, Neurosci. Res. 37, 21 (2000).

As the primary and the secondary antibody useful in the above-described immunohistochemical or immunocytochemical analysis and Western blotting, those listed in item 35) of the Notes provided later may be given.

The oligodendroglias or precursor cells thereof where FcRγ expression has been confirmed by the above-described method are judged to be capable of myelinogenesis. This judgment is applicable to the diagnosis of the degree of progress or the prognosis of treatment of diseases such as demyelinating diseases, dysmyelinating diseases and myelinoclasis. Briefly, if FcRγ-positive cells (oligodendroglias or precursor cells thereof) remain, the fact suggests that there is a possibility of myelin regeneration. Therefore, it is believed that stimulation treatment using a substance capable of activating FcRγ (e.g. anti-FcRγ antibody) would be effective. Or, when demyelination is so severe that repeated regeneration is hardly effective against continuous demyelination, it is considered that oligodendroglias or precursor cells thereof might possibly die out. Under such conditions, it is expected that FcRγ-positive cells have disappeared and that a stimulation treatment would not produce much effect. The more the FcRγ-positive cells are, the better the prognosis will be. However, those cases where mutations or abnormalities are found in the FcRγ-mediated signaling pathway are excluded as exceptions. In such cases, it is reasonable to consider that prognosis is bad because the pathway is not expected to function even if FcRγ-positive cells are present.

The present invention provides a method of examining FcRγ expression in animal brain tissues or cells by any of the following methods: immunohistochemical or immunocytochemical analysis, a gene amplification method, or Western blotting. These methods of the present invention are useful in detecting myelinogenetic oligodendroglias or precursor cells thereof. The oligodendroglias or precursor cells thereof where FcRγ expression has been confirmed are judged to be capable of myelinogenesis. This judgment is applicable to the diagnosis of the degree of progress or the prognosis of treatment of diseases such as demyelinating diseases, dysmyelinating diseases and myelinoclasis.

When FcRγ expression in animal brain tissues or cells is examined by immunohistochemical or immunocytochemical analysis or Western blotting, it is preferable to further examine the expression of at least one marker selected from the group consisting of PDGFαR, MAG, A2B5, 04, 01, MBP, PLP, DM-20, CNPase, MOG, NG2 and AN2 in oligodendroglias or precursor cells thereof.

Further, the present invention provides immunohistological or cell-staining reagent kits and Western blotting reagent kits, both types of kits comprising an anti-FcRγ antibody. These reagent kits may further comprise at least one antibody selected from the group consisting of anti-PDGFαR antibody, anti-MAG antibody, A2B5 antibody, 04 antibody, 01 antibody, anti-MBP antibody, anti-PLP antibody, anti-DM-20 antibody, anti-CNPase antibody, anti-MOG antibody, NG2 antibody and AN2 antibody. These antibodies may be prepared by the methods described in the review article of N. Bat & D. Pham-Dinh, Physiol. Rev., 81:871-927 (2001).

Anti-FcRγ antibody, anti-PDGFαR antibody, anti-MAG antibody, A2B5 antibody, 04 antibody, 01 antibody, anti- MBP antibody, anti-PLP antibody, anti-DM-20 antibody, anti-CNPase antibody, anti-MOG antibody, NG2 antibody and AN2 antibody may be labeled with a fluorescent dye, enzyme, heavy metal or the like (direct method). Alternatively, instead of labeling these antibodies (primary antibodies), secondary antibodies specific thereto may be labeled with a fluorescent dye, enzyme, heavy metal or the like (indirect method).

The immunohistological or cell-staining reagent kits of the invention may further comprise color formers (e.g. DAB), aqueous hydrogen peroxide (to be used for eliminating endogenous peroxidase and activating DAB), buffers (e.g. PBS (phosphate buffered saline), counter-staining dyes (e.g. methyl green), cover slips (plastic covers to be put on sections for reducing antibody consumption) and so on.

The Western blotting reagent kits of the invention may further comprise transferring buffers, blocking reagents, washing solutions, and so on.

The present invention also provides gene amplification reagent kits comprising at least a pair of primers capable of specifically amplifying the mRNA of FcRγ. The primers may be so designed that a specific region of the nucleotide sequence of FcRγ-mRNA of the relevant animal species (GenBank M33195 for human (SEQ ID NO: 15) and GenBank NM 010185 for mouse (SEQ ID NO: 17)) can be amplified specifically.

The primers are 15-30 nucleotides, preferably 20-25 nucleotides, in length. Specific examples of primers include a primer having the nucleotide sequence as show in SEQ ID NO: 1 and a primer having the nucleotide sequence as in SEQ ID NO: 2.

The gene amplification reagent kits of the invention may further comprise reverse transcriptases, DNA polymerases, RNase-free water, buffers, control mRNAs, control primer sets, dNTP mix, and so on.

By using the reagent kit of the invention, it is possible to examine FcRγ expression in animal brain tissues or cells.

The reagent kit of the invention may contain written instructions and may be wrapped. The instructions may teach how to use the kit and how to analyze results.

Hereinbelow, the present invention will be described specifically with reference to the following Examples. These Examples are provided for the purpose of illustration, and should not be construed as limiting the scope of the invention.

EXAMPLE 1

FcRγ Expression in Oligodendroglia in vitro

In the immune system, the activation of Src family tyrosine kinase signaling involves the interaction between molecules with cytoplasmic domains containing immunoreceptors tyrosine-based activation motifs (ITAM) (24; reviewed in 25). Src family tyrosine kinase phosphorylates the tyrosine residues within the ITAM, triggering intracellular signaling (26). Fyn, a member of the Src family, is critical in the initial events of myelination (9). This evidence suggests that an ITAM-bearing molecule, expressed in oligodendroglia during the initial events of myelination, may be involved in myelinogenesis. FcRγ, containing a cytoplasmic ITAM shown to be phosphorylated by Fyn (27), was examined as a candidate but this immunological molecule has not been previously shown to occur within oligodendroglial cells.

The following is the first report detailing the existence of FcRγ within the oligodendroglial lineage. Total RNA was extracted from cultured oligodendroglial precursor cells (OPC) (28,29) isolated from the mouse CNS but MAG had not yet been expressed at that stage (30). Significant expression of FcRγ mRNA, however, was detected by RT-PCR (31) at levels comparable to mast cells (FIG. 1A-a). CD3ζ, another ITAM-containing molecule. (21) involved in neural development and plasticity (32), was not detectable in OPC by RT-PCR (FIG. 1A-b).

The inventors have also detected the expression of FcRγ in A2B5-positive oligodendroglial precursor cells (33; FIG. 1B-b) as well as in O4- and O1-positive immature oligodendroglia (34; FIG. 1B-d,f) by immunocytochemistry. Therefore, FcRγ is expressed both at the mRNA and protein levels within OPC. Western blot analysis of cultured O4-positive immature oligodendroglia (37) also detected the presence of this molecule (FIG. 1C)

The expression of FcRγ within OPC and immature oligodendroglia, considering that this molecule couples to Fyn via ITAM (27), suggests that FcRγ may be involved in myelinogenesis in oligodendroglia.

EXAMPLE 2

FcRγ Expression in Oligodendroglia in vivo

In order to examine FcRγ expression within the CNS in vivo, the inventors preformed immunohistochemistry on the brains of neonatal mice at variable ages (36,38,39). FcRγ-positive cells were detectable at birth (P0) within the subventricular zone (germinal matrix areas adjacent to the cerebral ventricles; SVZ) (FIG. 2-a). Four days after birth (P4), the expression pattern expanded into the white matter, becoming detectable within the corpus callosum (FIG. 2-b). By P7, or the age at which MBP and MAG become detectable by a immunohistochemistry, FcRγ expression had been localized primarily to the white matter (FIG. 2-c). Interestingly, the expansion of the observed staining distribution strongly resembles the pattern of postnatal gliogenesis from SVZ (40). FcRγ-positive cells were also observed adjacent to the mouse-Musashi-1 (m-Msi-1)-positive neural stem cell layer of the lateral ventricle at P0 (41, FIG. 2d,e), suggesting that FcRγ-positive cells are differentiated from neural stem cells. In the adult CNS, the distribution was similar to that observed at P7 (FIG. 2-f). Therefore, FcRγ, is expressed in the CNS prior to the expression of MAG (early in the second postnatal week 6,20); also, this FcRγ-positive population is retained in the adult CNS. It was surprising that a restricted population of FcRγ-positive cells was observed within the adult CNS, with the distribution localized to the white matter in the supraventricular area and to the adult SVZ near the lateral ventricle (FIG. 2-f). The presence of these cells implies that gliogenesis in FcRγ-positive cells is maintained throughout adulthood or that the cells generated during the early postnatal period are quiescent within this region.

In order to confirm that those FcRγ-expressing cells are derived from the oligodendroglial lineage in vivo, the inventors labeled FcRγ-expressing cells with several antibodies and determined their identity (42). At P0, the FcRγ-expressing cells were distinct from both GFAP-positive cells (cells of the astroglial lineage) and Ox-42-positive cells (43; cells of the microglial lineage) (FIG. 3A). Although very few of the FcRγ-expressing cells co-stained weakly with GFAP within the SVZ, the majority of the cells were GFAP-negative. FcRγ-expressing cells did not co-labeled with Ox-42, showing that the majority of FcRγ-expressing cells at P0 do not arise from either the astroglial or microglial lineage. These cells are presumably derived from the oligodendroglial lineage. At P7, we detected FcRγ-expressing cells, co-labeled with Fyn (FIG. 3B-a) or MAG (FIG. 3B-b, 44). As MAG is expressed specifically for oligodendroglia (12), FcRγ-expressing cells evolve from the oligodendroglial lineage in vivo.

In the adult CNS, FcRγ-positive cells were observed within a restricted area of the white matter (FIG. 2-f). The inventors observed cells with an immature oligodendroglial morphology, staining for both FcRγ and MBP (FIG. 3C-a). This suggests the presence of FcRγ-positive, oligodendroglial cells within the adult CNS. In the contrast to early postnatal brains, a small subpopulation of GFAP-positive cells were also FcRγ-positive, predominantly within the adult SVZ (FIG. 3C-b). The majority of GFAP-positive cells were negative for FcRγ; this limited population of GFAP-FcRγ double-positive cells are unique within the adult CNS. It remains to be examined whether these cells are SVZ astrocytes that act as neural stem cells (45).

FcRγ is expressed both in vitro and in vivo prior to MAG expression in the oligodendroglial lineage. However, under microscopic examination, the expression of MAG and FcRγ did not co-localize completely within oligodendroglia at the pre-myelinating stage in vivo. MAG stained the edges of cellular processes strongly; FcRγ stained the cell membrane of the cellular body (FIG. 3B-b). Fyn was detected primarily in the cell membrane, giving a similar expression pattern to FcRγ as examined by co-staining (FIG. 33-a). The expression of Fyn within pre-myelinating oligodendroglia in vivo closely mimics that of FcRγ but not MAG. FcRγ-positive cells were rarely observed within the gray matter or the white matter except in the SVZ and the supraventricular area at any of the ages analyzed (FIG. 2-f). Taken in conjunction with the expansion of the observed staining distribution (FIG. 2-a,b,c) and previous studies of gliogenesis from SVZ (40), the above mentioned observation indicates that FcRγ is expressed within OPC or pre-myelinated oligodendroglia but not in mature myelinated cells.

Based on the assumption that FcRγ initially triggers myelinogenesis (i.e. triggers the Fyn-MBP cascade, 6), the inventors expected the expression of FcRγ to be similar to that of both Fyn and MBP. By examining serial sections, the invention observed similar staining patterns for FcRγ, Fyn, and MBP within enlarging myelin sheaths at P7 (FIG. 3D). Fyn is also expressed in the axon (46). The similarity in expression patterns suggests the relationship between these molecules. This evidence supports the role of FcRγ as the trigger of the Fyn-MBP cascade.

EXAMPLE 3

FcRγ Signaling Stimulates MBP Expression.

In order to examine the effect of FcRγ stimulation on the expression of MBP, the inventors artificially generated FcRγ signaling in OPC (28,29) by administration of an anti-FcRγ rabbit polyclonal antibody (47). Following 24 hours of the stimulation, cultured OPC with few processes demonstrated remarkable morphological changes to acquire well-developed processes (FIG. 4A-b). Such developments were not observed in the absence of the antibody (FIG. 4A-a). MBP expression was strongly stimulated by this signaling, as compared to controls in analysis by Western blotting (FIG. 4B; 48). Similar experiments on Fyn also showed increased expression in stimulated oligodendroglia (FIG. 4B). As Fyn is up-regulated two- to three-fold during oligodendroglial differentiation (19), the observations of the inventors, i.e. an up-regulation of Fyn expression and dramatic morphological changes, indicate that the FcRγ signaling induced OPC differentiation. The FcRγ signaling, therefore, is essential for myelinogenesis, subsequently stimulating the expression of MBP in oligodendroglia and up-regulating Fyn expression.

The stimulation of MBP expression predominantly up-regulated the exon 2-containing isoforms (FIG. 4B). Four major isoforms of MBP, producing proteins of 14.0, 17.0, 18.5 and 21.5 kD, are generated by selective use of seven exons within the MBP gene (49). Although precise role of each isoform remains to be investigated, these isoforms can be divided into two groups by their distribution within the cell. The exon-2-containing isoforms, i.e. the 17.0 and 21.5 kD proteins, distribute diffusely throughout the cytoplasm; these isoforms commonly accumulate in the nucleus whereas the two remaining isoforms are found mainly at the plasma membrane, playing a role in myelin compaction (8). The active transport of exon 2-containing isoforms into the nucleus suggests that these isoforms may play a regulatory role in myelination (50); the observations of the inventors support this possibility. The role of the exon 2-containing isoforms of MBP also supports the inventors' proposal that FcRγ is responsible for triggering myelinogenesis.

Figure 7:
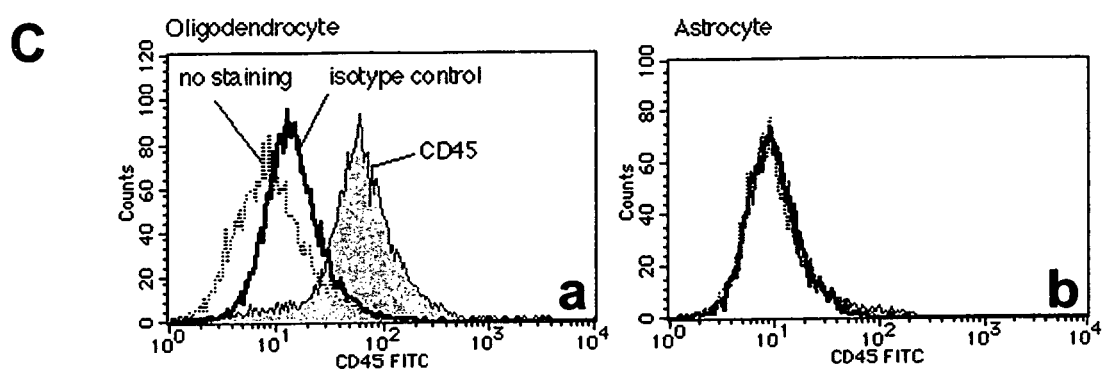
FIG. 7 shows co-expression of FcγRI/III and CD45 with FcRγ in oligodendroglia. A: RT-PCR analysis of immature oligodendroglia (37) detected the alpha chain of FcγRI/III, but not the alpha chain of FcεRI, suggesting that the partner of FcRγ is the IgG-specific Fc receptor. Semi-quantitative RT-PCR revealed approximately 1.8-fold (FcγRI) and 0.8-fold (FcγRIII) mRNA expressions in immature oligodendroglia, relative to the expression in bone marrow-derived mast cells (data not shown). B: CD45 is expressed in MAG-positive cells (arrowheads). This means CD45 is expressed in oligodendroglia (c). CD45 is co-expressed with Fyn in oligodendroglia during the initial stage of myelinogenesis at P10 (arrowheads; b). CD45 is also co-expressed with FcRγ in enlarging myelin sheaths at P7 (arrowheads; d) and in the adult CNS (arrowheads; a). All images were obtained from the white matter of the CNS (a is the border area between the white matter and the adult SVZ; b and d are from the corpus callosum, and c is from the anterior commisure). Bar: 25 µm. C: CD45 was detected easily by flow cytometry in cultured immature oligodendroglia (37) but not in astrocytes. These results suggest that CD45 is involved in the regulation of the signaling cascade proposed by the present inventors.

The inventors observed similar up-regulation of exon2-containing MBP isoforms and dramatic morphological differentiations following administration of the 2b isoform of mouse immunoglobulin G (IgG2b) in place of the anti-FcRγ antibody (FIG. 4B). The IgG2b monoclonal antibody used possesses an epitope that is not naturally found in mice (47). This antibody does not react with any oligodendroglial proteins in flow cytometry (data not shown). The stimulated expression of axon 2-containing MBP isoforms, therefore, suggests that IgG2b interacts with Fc receptors for IgG (FcγRs; FIG. 7A). The inventors failed to observe stimulation of Fyn expression following IgG2b administration (FIG. 4B), probably because the use of IgG2b is more indirect than that of the anti-FcRγ antibody as a stimulation technique.

The inventors have further stimulated OPC derived from FcRγ-deficient mice (58). Similarly administered IgG2b, however, failed to differentiate those OPC in contrast to the changes observed in wild type OPC (FIG. 4C). These results suggest that FcRγ is an essential signaling molecule for the differentiation of OPC and indicate that IgG2b certainly activated FcRγ via FcγRs.

EXAMPLE 4

Comparison Between FcRγ-, Fyn- and MBP-Deficient Mice

FcRγ and Fyn may be considered to co-operate in oligodendroglia to stimulate MBP expression. Phosphorylation of the FcRγ ITAM requires interactions with Src family tyrosine kinases (26). Among the Src family members, only five are expressed within the CNS (51). Of those five members, only Src, Fyn, and Lyn are expressed within oligodendroglia (52). Fyn, however, is the only Src family member essential for myelinogenesis (52). Fyn has been shown to be responsible for the ITAM phosphorylation of FcRγ (27). Therefore, the activation of FcRγ within oligodendroglia, which resulted in the up-regulation of MBP expression (FIG. 4B) depends on the phosphorylation of the ITAM by Fyn (27). Abolition of Fyn tyrosine kinase activity by a point mutation results in a severe myelin deficiency, similar to that observed in the absence of Fyn. This suggests that Fyn kinase activity is essential for myelinogenesis (52). Stimulation of MBP expression depends predominantly on Fyn (10), consistent with the results in vitro of the inventors (FIG. 4B).

In order to further examine the FcRγ-Fyn-MBP cascade in vivo, the inventors analyzed mutant mice deficient in either FcRγ, Fyn, or MBP (39). The most intense period of oligodendroglial proliferation occurs during the first 9 days after birth (53); oligodendroglias predominantly express exon 2-containing MBP at this age (8). The in vitro stimulation results of the inventors suggest that analysis of the myelination program at this age may reveal defects in myelinogenesis. The inventors therefore analyzed the brains of mice 10 days after birth and examined the initial stages of myelination. Immunohistochemical analysis of the white matter of FcRγ-, Fyn-, and MBP-deficient mice (36,38,39) revealed a similar delay in myelinogenesis in the three mutants, as compared with age-matched wild type nice. The restricted expression of MBP and/or MAG observed in all mutants (FIG. 5A) indicates that these three molecules are indispensable in myelinogenesis. Western blotting analysis of FcRγ- and Fyn-deficient mice revealed a decrease in MBP expression both in neonates at P10 and in adults (FIG. 5B; 48). These observations suggest that the FcRγ-Fyn-MBP cascade is pivotal in the initial stages of myelinogenesis in vivo.

Figure 4:
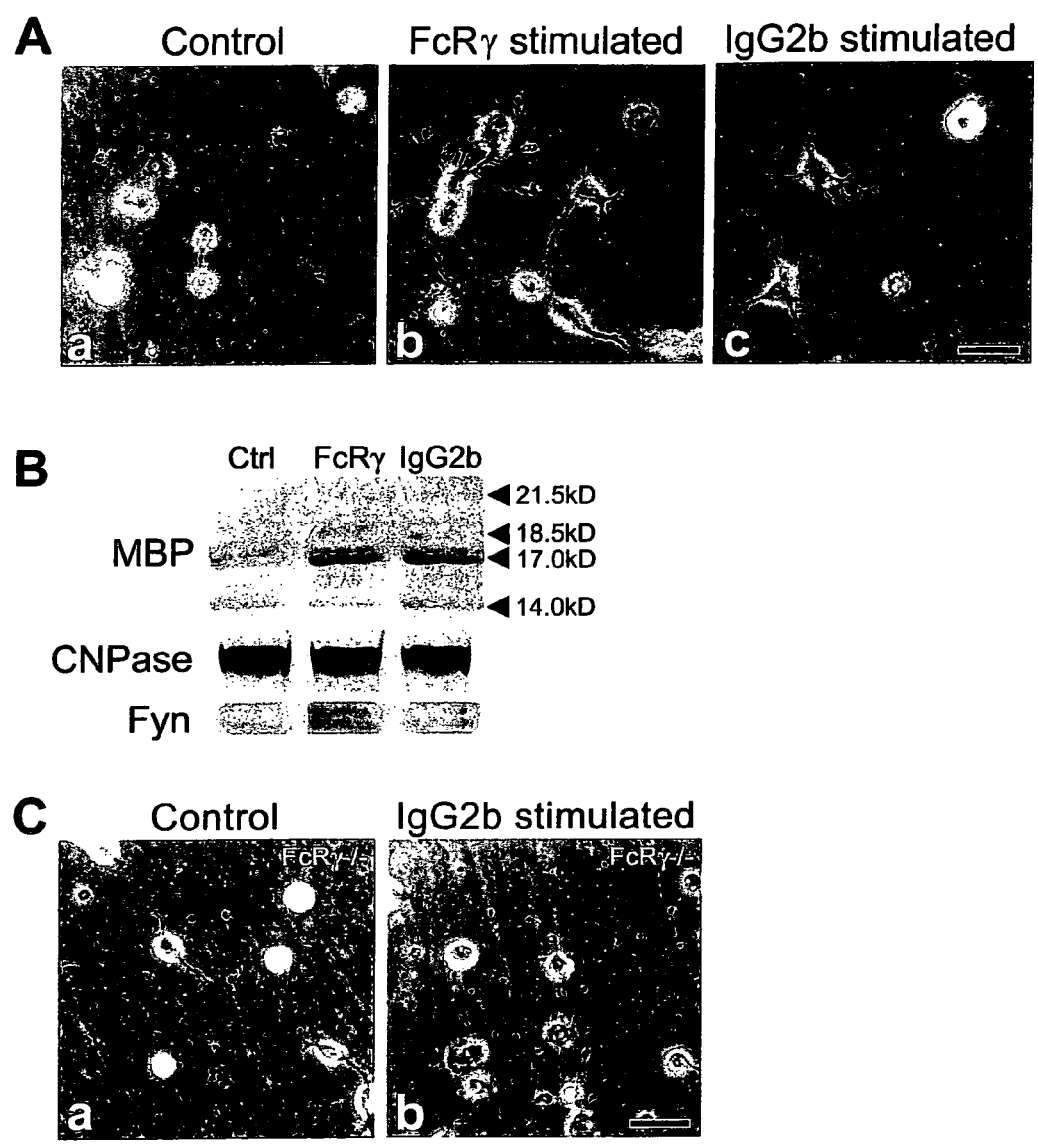
FIG. 4 shows activation of FcRγ in vitro. A: Following stimulation with an anti-FcRγ antibody for 24 hrs, OPC demonstrated dramatic morphological changes, extending well-developed processes (b). Similar change were observed when IgG2b, of which epitope is not naturally found in mice (47), was substituted for the antibody (c). These were not observed without stimulation (a). Bar: 35 µm. B: Western blotting analysis of MBP and Fyn expression. Cells seen in Panel A were lysed and analyzed. MBP, predominantly the exon-2 containing isoforms. (17.0 kD and 21.5 kD), and Fyn were up-regulated in OPC following stimulation with anti-FcRγ antibody (FcRγ; lane 2), as compared to OPC without an activation stimulus (ctrl; lane 1). Stimulation with IgG2. (IgG2b; lane 3) via Fc receptors for IgG, also up-regulated MBP expression but no obvious changes in Fyn were observed; this probably reflects the indirectness of the stimulation process. CNPase, a marker for both OPC and differentiated oligodendroglia, was used as a loading control. C: IgG2b fails to stimulate OPC derived from FcRγ-deficient mice (FcRγ−/−) (58; compare b with a), indicating that the changes in OPC as seen in Panel A are dependant on FcRγ expression in the cell. Bar: 35 µm.

Quantitation of the Western blotting results (54) revealed that the total amount of MBP in the adult CNS had decreased to 40.3% and 60.8% of the wild-type level in Fyn-deficient and FcRγ-deficient aninals, respectively. The expression of exon 2-containing MBP (the sum for 21.5 kD and 17.0 kD) was found to be more severely affected than the expression of the two other isoforms; levels of these isoforms had decreased to 31.9%; and 40.0% of the wild-type level in Fyn-deficient and FcRγ-deficient mice, respectively. The similar patterns observed in FcRγ- and Fyn-deficient mice support the present inventors' theory that these molecules are involved in the signaling cascade that regulates myelinogenesis. The predominant decrease in exon 2-containing MBP levels in both mutants supports the in vitro results of the inventors, also suggesting these isoforms in this process (FIG. 4).

Histological comparison of MAG expression at P10 in the mutants revealed that the distribution of MAG-positive immature oligodendroglia (6) is more reduced in MBP-deficient mice than in FcRγ-deficient mice (FIG. 5A-e,f,g) Fyn-deficient mice displayed an intermediate phenotype. In the three mutants, the number of MAG-positive immature oligodendroglias that had migrated into the cerebral cortex from the corpus callosum by P10 (55) was approximately 44%, 25%, and 12% of the wild type level for the FcRγ-, Fyn-, and MBP-deficient mice, respectively (FIG. 5C). This result correlates linearly to the levels of MBP, suggesting that MBPs, especially the exon 2-containing isoforms, are essential in myelinogenesis.

EXAMPLE 5

Dysmyelination in the Absence of FcRγ

In order to examine myelination in the absence of FcRγ, the inventors analyzed FcRγ-deficient mice at several ages. The disturbance in myelination observed at P10 (FIG. 5) may have resulted from a failure of gliogenesis; in order to address this possibility, the inventors analyzed the expression of PDG-FαR a marker for the earliest progenitors of the oligodendroglial lineage (56). FcRγ co-stained with PDGFαR-positive cells in the white matter at P10 (FIG. 6A-a), indicating that FcRγ is expressed within cells of the oligodendroglial lineage (FIG. 3). Only a fraction of the PDGFαR-positive cells, however, co-stained with FcRγ (FIG. 6A-a). FcRγ-positive cells were also PDGFαR-positive (FIG. 6A-a), suggesting that PDGFαR-positive/FcRγ-negative cells may be quiescent glial precursor cells within the CNS. PDGFαR may also serve as a useful marker for examining the state of gliogenesis in the experiments of the inventors. At P10, or the age at which they observed a myelination deficiency (FIG. 5), the inventors did not observe changes in the number or distribution of PDG-FαR-positive cells (FIG. 6A-b, c). The defect in myelination observed at P10 (FIG. 5), therefore, resulted primarily from a disturbance in myelinogenesis, not in gliogenesis.

In order to determine whether the defect observed at P10 (FIG. 5) would be compensated later stages by the living samples, the inventors counted the number of MAG-positive immature oligodendroglias (6) at later stages of development (55). Differences in the numbers of MAG-positive immature oligodendroglias between the mutant and the wild type became insignificant at later stages of development (FIG. 6B-a). At this point, however, myelination was still defective in the mutant mice. At P50, in addition to MBP, the expression of proteolipid protein (PLP), a major protein component of myelin, was also found to decrease in the mutant as compared with the wild type by immunohistochemical analysis (FIG. 6B-b, c; a part of data not show), reflecting a generalized myelination defect even at later stages of development. The electron microscopy (57) of the corpus callosum at P67 revealed severely hypomyelinated axons in the dorsal region (FIG. 6C-a, b). Surprisingly, severe axonal swelling was also observed in the ventral region (FIG. 6C-c, d) It is known that myelin deficiency, especially in the presence of reduced PLP, causes axonal swelling (1). These electron microscopic observations show a severe ad generalized myelin deficit in the absence of FcRγ. In the mutants, the observed defect in myelination is not simply a delay, but a generalized hypomyelination that lasts throughout the later stages.

These observations show that FcRγ is essential in myelinogenesis, not in gliogenesis and support the inventors' theory that FcRγ triggers myelinogenesis both in vitro and in vivo.

EXAMPLE 6

FcγRs and CD45 Co-Expression with FcRγ

FcRγ is common to several immunoreceptors (21). Elucidation of the receptors involved in FcRγ activation in oligodendroglia is essential to understanding the molecular mechanism of myelinogenesis. FcRγ-deficient mice have been shown to be unable to express the alpha chain (i.e. ligand binding subunits) of both the IGE Fc re r (FcεRI) an the IgG Fc receptors (FcγRI/III) on the cell surface (58). The disturbed myelinogenesis in the mutant may have resulted from the lack of both FcRγ and those alpha chains. RT-PCR analysis of immature oligodendroglia in wild type mice (31) could not detect the alpha chain of FcεRI. Alternatively, the alpha chains of FcγRI and FcγRIII were easily detectable (FIG. 7A). These expression patterns were also confirmed by flow cytometry (data not shown). Therefore, Fc receptors specific to IgG, not those recognizing IgE, may be involved in myelinogenesis. The inventors cannot, however, exclude the possibility that other oligodendroglia-specific receptor(s) which share FcRγ may be involved. The in vitro studies of the inventors demonstrated that regardless of the receptor type, the activation of FcRγ can stimulate MBP expression (FIG. 4). Both the presence of maternal IgG in newborn mice, transferred via neonatal FcR (FcRn, reviewed in 59), and the existence of IgG-secreting cells in the immune system as early as at P7 (60) will support this conclusion. The in vitro stimulation study the inventors made using IgG2b resulted in the up-regulation of MBP levels (FIG. 4) and this is also consistent with their hypothesis.

CD45, a protein tyrosine phosphatase, regulates FcRγ signaling (reviewed in 61). CD45 dephosphorylates the inhibitory site of Src family tyrosine kinases, including Fyn. With CD45, Fyn remains inactive due to phosphorylation of the inhibitory site (61); signaling via FcRγ would not proceed in the absence of this signaling molecule. CD45, also known as leukocyte common antigen, is expressed specifically within the cells of immune system. The expression of this molecule within oligodendroglia has yet to be reported. The inventors have immunohistochemically double-stained the brains of mice at 7 days after birth (P7), at 10 days (P10) or adult mice (36,38,42) and discovered cells that co-expressed CD45 and MAG (FIG. 7B-c); as MAG is specifically expressed in oligodendroglia (12), the fining of co-expression demonstrates that CD45 is expressed within oligodendroglia. This expression pattern, including the absence of CD45in astrocytes, was confirmed by flow cytometry (FIG. 7C). Co-expression of CD45 and Fyn prior to the initial steps in myelinogenesis was confirmed in viva (FIG. 7B-b). These results indicate that CD45 is required for the activation of Fyn. CD45 was detected in both the enlarging, FcRγ-positive myelin sheath both at P7 (FIG. 7B-d) and in the adult CNS (FIG. 7B-a). Therefore, CD45 may play a regulatory role in the FcRγ-Fyn-MBP cascade both during the postnatal developmental stages in which myelin is rapidly generated and in the adult, especially during remyelination.

EXAMPLE 7

FcRγ-Fyn Double-deficient Mice

Purpose) It is in immunology that FcRγ and Fyn co-operate with each other. If they actually co-operate in myelinogenesis in the brain, FcRγ-Fyn double-deficient animals would exhibit severer symptoms. Based on this prediction, the inventors performed experiments. There are two interpretations for double deficiency. First, contemplate a cascade of A→B→C. If this is truly one cascade, the result (e.g. decrease in C) would be the same whether A or B or both A and B are knocked out. In actual organisms, however, it is considered that a number of cascades are mixed, or if one mechanism is knocked out, it will be compensated by another mechanism. Based on this assumption, deficiency of B would lead to severer symptoms than deficiency of A (since B is closer to C, compensation mechanisms will have less chance to work); or deficiency of both A and B would lead to the severest symptoms.

Methods) FcRγ-deficient mice (39, 58) were mated with Fyn-deficient mice (39, 46) to prepare FcRγ±Fyn± mice (F1 generation). Mating among the resultant F1 mice should yield FcRγ-/-Fyn-/- double-deficient mice (F2 generation) at a probability of 1/16. However, the probability was too low to yield the double deficiency. Therefore, FcRγ-/-Fyn± and FcRγ±Fyn-/- mice were selected from the F2 mice (genotypes were confirmed by extracting DNA from the tail vein and performing PCR), and mated with each other. The resulting F3 generation is to have FcRγ-/-Fyn-/- mice at a probability of 1/4. Since one mouse produces about 7 offspring mice per delivery, it is expected that some members of a litter would be the double deficiency mice. Actually, probably due to serious immunodeficiency (it is expected that FcRγ-Fyn double-knock out would destroy the immune system, causing embryonic or neonatal death) or perhaps due to cerebral malformation, the double-deficient mouse could be obtained at the chance of once in several deliveries, though the probability was considerably low. At present, the inventors are trying to obtain double-deficient F4 generation mice at a probability of 1/1 by mating F3 double-deficient mice among themselves but the efficiency is rather low. F3 mice were used in the experiment. Briefly, the resultant double-deficient mice at P10 were fixed with acid-alcohol, embedded in paraffin and then sliced into sections 10 µm thick. The expressions of MBP and MAG were examined by immunohistochemical techniques. Nissl staining for endoplasmic reticula was also performed to examine the structure of the brain roughly. Similar experiments were also conducted on mice at 1.5 months after birth (young adult).

Figure 9:
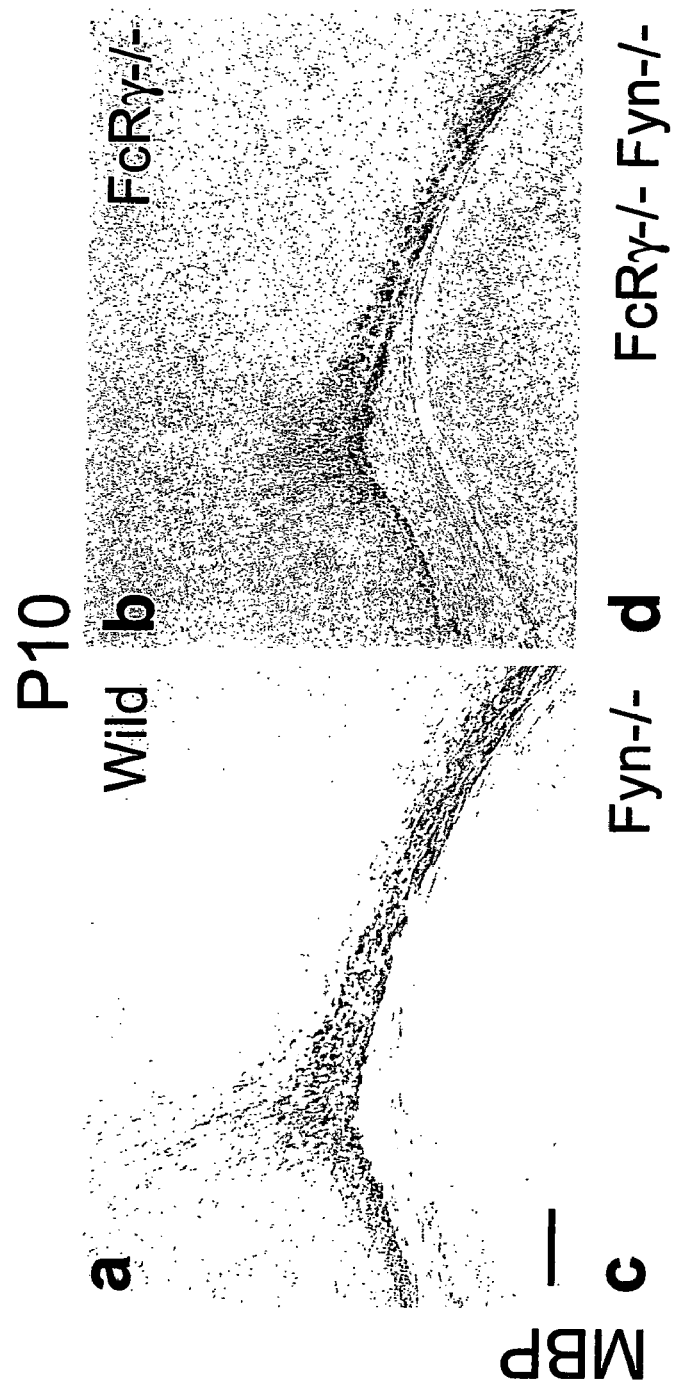
FIG. 9(a-d) shows immunohistochemical staining of MBP in 10-day old mouse brains. "Wild", "FcRγ-/-", "Fyn-/-" and "FcRγ-/-Fyn-/-" appearing at the upper right corner of individual images represent genotypes. All the mice are of C57B1/6 lineage. The cerebral area from the corpus callosum to the cingulum is photographed. The oval-shaped structure appearing in the lower part of each image represents the hippocampus. As shown in these images, MBP expression levels decrease in the following order: Wild> FcRγ-/->Fyn-/->FcRγ-/-Fyn-/-.

Results) The results of comparison of wild-type (Wt), Fyn-/-, FcRγ-/- and FcRγ-/-Fyn-/- at P10 showed that the expression levels of both MBP and MAG, decreased in the following order: Wt>FcRγ-/->Fyn-/->FcRγ-/-Fyn-/- (FIGS. 9, 10). Therefore, co-operation of FcRγ with Fyn was confirmed. Nissl staining at P10 exhibited expansion of the ventricle and malformation of the fornix. Nissl staining at the age of 1.5 months clearly showed serious ventricular expansion (hypocephalus), malformation of the hippocampus and malformation of the fornix (FIG. 11e-h). MBP staining at this age gave results that were by no means similar to those at P10; on the contrary, it was confirmed that the double-deficient mice had little myelin in the cerebral cortex (FIG. 11a-d). These results were verified in other experiments using other myelin proteins such as PLP.

Conclusion) It was confirmed that FcRγ and Fyn also co-operate with each other in myelinogenesis in the brain.

EXAMPLE 8

CD45 Deficient Mice

Purpose) CD45 is expressed in oligodendroglia, as confirmed in Example 6, and CD45 is known in immunology as an activator of Fyn. Therefore, the inventors speculated that CD45 might play some role in myelinogenesis in oligodendroglia. In addition, since genetic mutations of CD45 were found in multiple sclerosis (MS), the inventors also speculated that abnormalities in oligodendroglia might be in part the etiology of Ms. (However, the CD45 abnormalities found in MS so far are not mutations that eliminate CD45 completely but they are mutations that disturb the expression pattern of some isoforms of CD45 or reduce the total amount of expression of CD45.) With respect to the CD45 mutations in MS patients, negative papers have later been submitted, and the issue has not yet been settled. In order to leave no question about this issue, the present inventors attempted to examine whether the myelinogenesis in oligodendroglia would be inhibited in CD45-deficient mice.

Methods) Mice lacking exon 6 of CD45 (thus expressing almost no CD45) were a kind gift from Dr. Kenji Kishihara, Kyushu University. This mouse was originally described in the following article.

Cell July 1993 16:74 (1) :143-56 "Normal B lymphocyte development but impaired T cell maturation in CD45-exon 6 protein tyrosine phosphatase-deficient mice", Kishihara K., Penninger J., Wallace V. A., Kundig T. M., Kawai K., Wakeham A., Tims E., Preffer K., Ohashi P. S., Thomas M. L. et al.

Brains from these mice were fixed at P10, sliced and had MBP and MAG stained by immunohistochemical techniques to examine expression levels of myelin. Further, brains were ground and subjected to Western blotting to examine expression levels of MBP. Brains from Fyn-deficient mice (P10) were also fixed and sliced in the same manner, followed by immunohistochemical staining for MAG so as to examine whether they would exhibit reduced myelin expression as in CD45-deficient mice (if CD45 is an activator of Fyn, similar reduction is expected). Further, oligodendroglial precursor cells (OPC) from the CD45-deficient mice were cultured and stimulated with an anti-FcRγ antibody or IgG so as to observe any responses (morphological changes and increase in MBP expression). In addition, in order to demonstrate that CD45 was actually expressed in oligodendroglia, staining of the cultured OPC and histological staining (double-staining with MAG, a marker for oligodendroglia) were performed. In order to confirm that the antibody to CD45 actually reacted with CD45, causing no cross-reaction with something else, CD45 staining was performed on the CD45-deficient mice.

Results) The CD45-deficient mice at P10 showed apparent decrease in myelinogenesis (FIG. 13, c-e). The degree of this decrease was similar to that seen in Fyn-deficient mice (FIG. 13, c and f-h). Further, it was confirmed that OPC from the CD45-deficient mice exhibited no response to either anti-FcRγ antibody or IgG (FIG. 13, a and b). These results confirm that the differentiation of OPC to oligodendroglia is inhibited by CD45 deficiency. The actual expression of CD45 in oligodendroglia was demonstrated by histological double-staining with MAG (FIG. 12, d) and by the staining of OPC (FIG. 12, a and b). Absence of the cross-reaction was demonstrated by the result that tissues from CD45-deficient mice were not stained with the same antibody (FIG. 12, e).

Conclusion) Being expressed in OPC and immature oligodendroglia, CD45 was confirmed to be necessary at the stage when OPC is differentiated into myelin-forming oligodendroglia.

EXAMPLE 9

IgG-Deficient Mice

Purpose) In Example 3, it was shown that FcRγ is the trigger of myelinogenesis but in the actual adult body, FcRγ is one of the signaling molecules of immunoglobulin Fc receptors such as FcγRI or FcγRIII. Therapeutically, FcRγ may be stimulated directly, but under physiological environments, the intended mechanism is expected to work as follows: IgG binds to FcγRI or FcγRIII, thereby stimulating FcRγ. IgG is supplied from the mother's body via the placenta, or contained in mother's milk. Since the blood-brain barrier (BBB) between the brain and vessels is immature at fetal to infantile stages, IgG is capable of entering the brain. Conversely, an adult has BBB and IgG does not enter the brain, probably preventing excessive myelination. As a matter of fact, the BBB is destroyed in MS patients, probably reflecting demyelination. The destruction may have occurred in order to introduce IgG into the brain and regenerate myelin. In order to say such stories are valid, it is necessary to prove that IgG actually has such a function. Certainly, it has been confirmed in immunology that FcRγ co-operates with FcγRI/RIII and that both FcγRI and FcγRIII are detected in oligodendroglia. Thus, coupling to IgG is expected in all likelihood. However, there is a possibility that some other molecule couples to FcγRI/RIII in the brain. In order to prove the necessity of IgG, the inventor analyzed mice that had been genetically engineered to lose the IgG producing ability. Fyn and FcRγ of the mice are normal function and expression.

Methods) IgG-deficient µMT mice were purchased from Jackson Laboratory (it appears that the mice are also IgM-deficient; this, however, would not effect the experiment since IgM does not pass through the placenta nor is it little contained in mother's milk.) The original mouse is described in the following reference.

Nature 350:423-426 (1991)

Kitamuta D., Roes J., Kuhn R., Rajewsky K., 1991.

A B cell-deficient mouse by targeted disruption of the membrane exon of the immunoglobulin mu chain gene.

These mice were immunohistochemically stained for MAG at P7, P10 and P50, and compared with wild-type (Wt) mice.

Results) As expected, myelin decreased to Wt at any of P7, P10 and P50 (FIGS. 15, 16, 17). The results at P7 and P10 suggest that IgG from the mother's body is important for myelinogenesis (at these stages, mice can hardly produce IgG by themselves; anyway, µMT mice, both mothers and child mice, used in the experiment are incapable of producing IgG.)

Conclusion) The importance of FcRγ for in vivo myelinogenesis in oligodendroglia is as described above. The experiment revealed that IgG is a physiological trigger of the myelinogenesis.

Discussion

Figure 5:
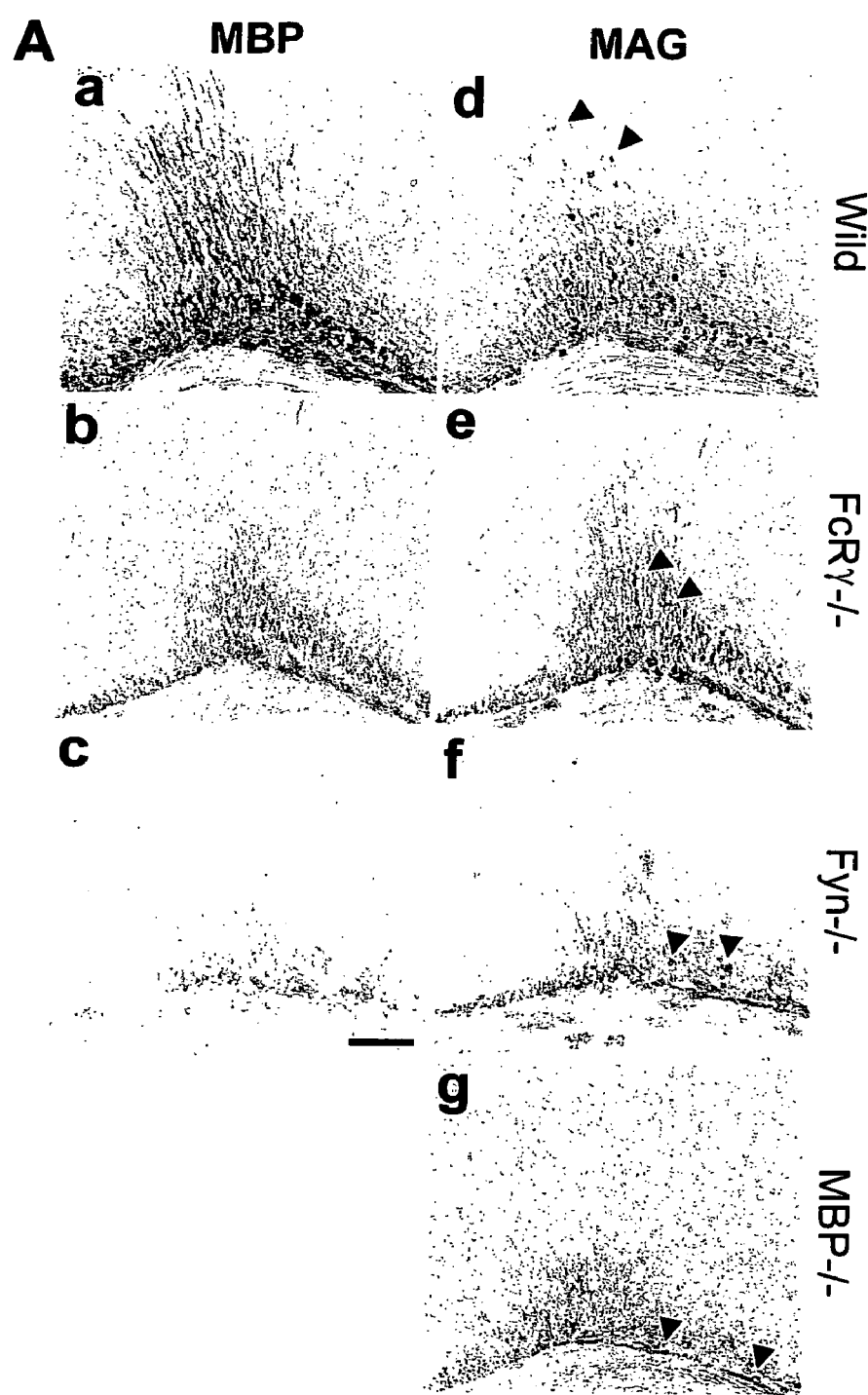
FIG. 5 shows comparison of wild type (Wt), FcRγ-deficient (FcRγ−/−), Fyn-deficient (Fyn−/−), and MBP-deficient (MBP−/−) mice. A: Coronal sections of the cerebrum are shown at P10. a-d, b-e, and c-f are adjacent sections. The white matter of the cingulum where morphologies of myelin and myelinating oligodendroglia are discernible is selected and photographed. The distribution of MBP is restricted in FcRγ- (b) and Fyn-deficient mice (c), the Fyn-deficient mice showing a more severe phenotype (c). The distribution of MAG-positive immature oligodendroglia (arrowheads) is restricted in all three mutants. The MBP-deficient mice display the most restricted phenotype (g); Fyn-deficient mice have an intermediate phenotype (f); FcRγ-deficient mice are the least affected (e). These observations indicate the existence of FcRγ-Fyn-MBP cascade within myelinating oligodendroglia. Bar: 100 µm. B: Western blotting analysis of MBP in myelin fractions. MBP is reduced in Fyn- and FcRγ-deficient mice at P10 (a) as well as in the adult (b). In the adult CNS, the total of MBP is reduced to 40.3% and 60.8% of the wild-type level in Fyn- and FcRγ-deficient mice, respectively (54). Reduction in the exon-2 containing MBP isoforms (17.0 kD and 21.5 kD)) was severer than in the remaining isoforms and it decreased to 31.9% and 40.0% of the wild-type level in Fyn- and FcRγ-deficient adult mice, respectively (54). These results correlate with the in vitro results (FIG. 4). C: MAG-positive immature oligodendroglia (6), which have migrated into the cortex by P10, visualized in each coronal section, are analyzed statistically (55). The cell counts per slice were approximately 44%, 25%, and 12% of the wild type cell count in FcRγ-, Fyn-, and MBP-deficient mice, respecively. This indicates that exon-2 containing MBP isoforms are important for myelinogenesis.
Figure 6:
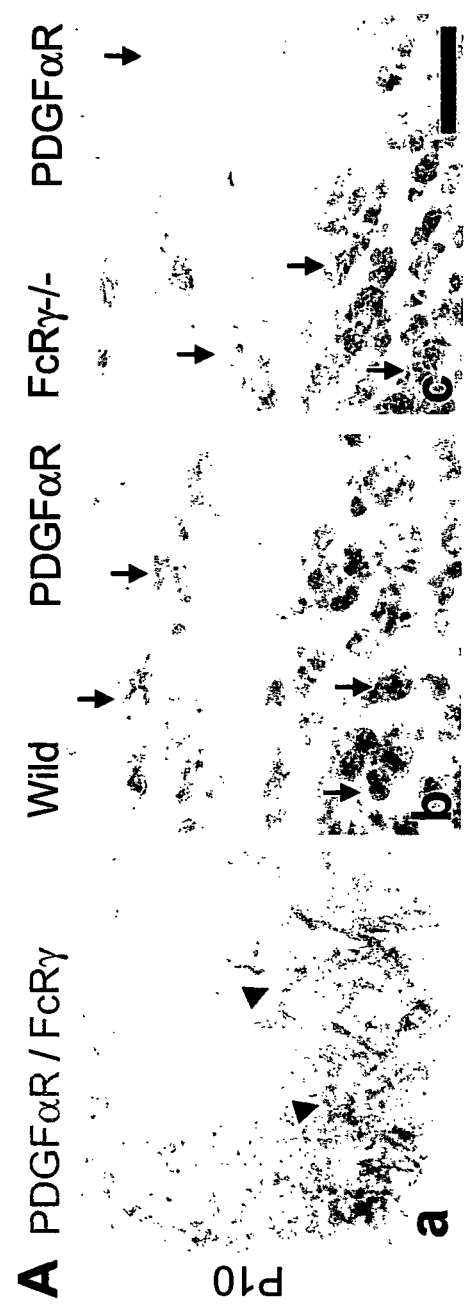
FIG. 6 shows dysmyelination in the absence of FcRγ. A: FcRγ is co-stained with PDGF-αR, a marker for OPC (56), in the optic nerve (arrowheads; a), showing FcRγ is expressed in the oligodendroglial lineage cells. No significant differences in the distribution of PDGF-αR-positive cells (arrows) are recognized between FcRγ-deficient (FcRγ−/−) (c) and wild type (b) mice at P10. The between the SVZ and the white matter is shown. These observations indicate that the initial defect in myelinogenesis as observed at P10 (FIG. 5) results primarily from a failure in myelinogenesis, not in gliogenesis. b and c are counter-stained with methyl green. Bar: 40 µm. B: Statistical analysis of MAG-positive oligodendroglia (6, 55) at later stages of development revealed no remarkable differences between cell numbers at P50 and P90 (a). Even at those times, however, myelin abnormalities were evident; immunohistochemical analysis demonstrated that the levels of MBP (data not shown; see FIG. 5B-b) and PLP in the corpus callosum at P50 were reduced in staining intensity in FcRγ-deficient (c) as compared to the wild type (b). Bar: 40 µm. C: Electron microscopy revealed severe hypomyelination in the dorsal corpus callosum of FcRγ-deficient mice (b), as compared with wild type mice (a) at P67. The ventral corpus callosum of FcRγ-deficient mice displays severe axonal swelling (asterisks) of hypomyelinated axons (d), as compared to the wild type (c). Bar: 2 µm (b), 500 nm (d).
Figure 6:
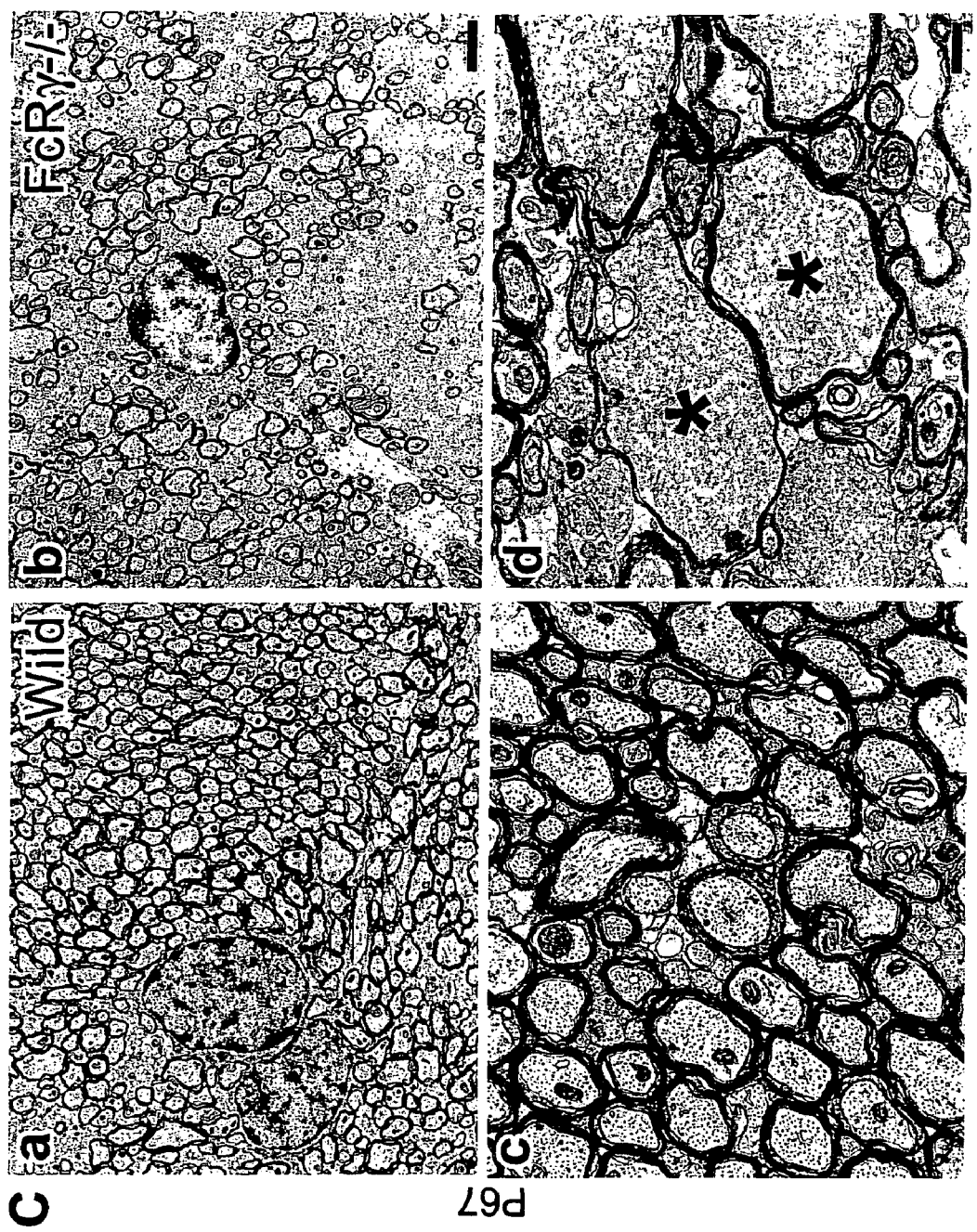
Figure 8:
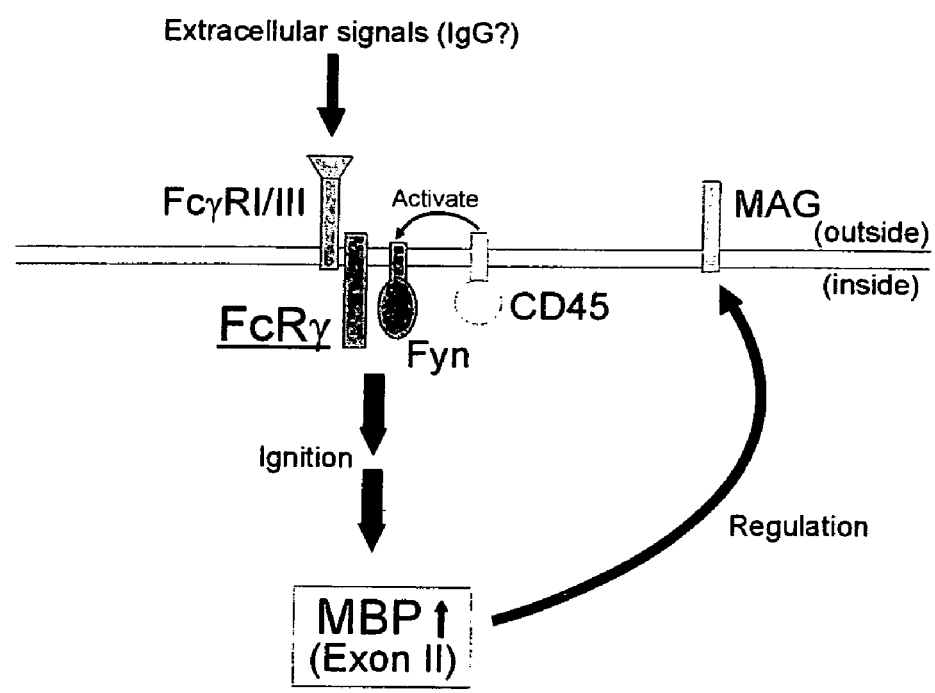
FIG. 8 shows the mechanism of myelinogenesis proposed by the present inventors. An extracellular signal, such as IgG, triggers FcRγ through its association with an Fc receptor specific to IgG (FcγRI/III). CD45 first activates Fyn. Then, the ITAM phosphorylation of FcRγ proceeds, utilizing Fyn as a tyrosine kinase. This signal consequently stimulates the expression of MBP, particularly the exon-2 containing isoforms. MBP contributes to the regulation of MAG expression as previously reported (6) Polymorphisms in FcγRs (66) and mutations in CD45 (23) are reported to be present in sane populations of MS patients. This model can explain both the mechanism of demyelination and the efficacy of IVIg therapy on demyelinating diseases (62). Direct stimulation of FcRγ (FIG. 4) may in future prove to be an effective treatment that will enhance remyelination.

A model summarizing the mechanism of myelinogenesis proposed by the present inventors is shown in FIG. 8. FcRγ is expressed both in vitro and in vivo in cells of the oligodendroglial lineage (FIGS. 1-3). Here, the inventors propose that FcRγ triggers myelinogenesis. Through a functional co-operation with Fyn (27), FcRγ induces both morphological differentiation and an up-regulation of MBP expression (especially the expression of those isoforms containing exon 2) (FIG. 4). The model was confirmed in vivo by the fact that FcRγ-deficient mice show severe deficit in myelinogenesis although they show no significant changes in oligodendroglial production (FIG. 6). The mutants also exhibit decreases in MBP expression, with more serious decreases in the expression of the exon 2-containing isoforms (FIG. 5). The expression of Fc receptors specific for IgG, not for IgE (FIG. 7A), suggests a possible role of IgG as an extracellular triggering molecule that activates Fc receptors on oligodendroglia. In vitro stimulation with IgG caused dramatic morphological differentiations in wild type OPC, but not in FcRγ-deficient OPC (FIG. 4). In addition, CD45was co-expressed with Fyn and FcRγ within oligodendroglia during the initial stages of myelinogenesis (FIG. 7B, C), suggesting that CD45may regulate the activation of Fyn that is necessary for myelinogenesis. Mutations in CD45are reportedly involved in the development of MS in some populations (23).

IgG2b promotes the expression of MBP and morphological differentiations of OPC in vitro (FIG. 4). In order to support the IgG's physiological role of triggering myelinogenesis, it is expected that IgG is present prior to myelinogenesis. In addition to the maternally-derived IgG in neonatal mice (59), IgG-secreting cells are detectable in both the thymus and spleen by P7. These cells rapidly proliferate at this age (60). The initiation of myelinogenesis by IgG signaling via Fc receptors on oligodendroglia may explain the efficacy of intravenous immunoglobulin therapy (IVIg) against demyelinating diseases. Administration of high-dose IVIg is a highly successful treatment regimen for patients with demyelination diseases (reviewed in 62). In MS, IVg reduces the relapse rate (63). The mechanism of this treatment, however, has not been clarified. In animal models, imunoglobulins can promote remyelination within the CNS after demyelination that results from Theiler's virus infection (64). The ability of imunoglobulins to induce remyelination is mediated by the Fc portion of their molecule; F(ab')2 fragments can not induce these effects in animal models (65). These findings suggest that the ability of IVIg to promote remyelination may be mediated via the Fc portions of imunoglobulins, possibly activating the FcRγ-Fyn-MBP cascade within oligodendroglia. Polymorphisms in FcγRs influence the disability resulting from MS; MS patients carrying FcγRs with a higher affinity for IgG have a better clinical outcome (66).

Type IIB FcγR (FcγRIIB) is a unique inhibitory Fc receptor that interacts with IgG (reviewed in 67). This receptor may negatively regulate the FcRγ-Fyn-MBP cascade, resulting in diminished ability of polyclonal IVIg to promote myelinogenesis. The inventors confirmed the expression of FcγRIIB in cultured oligodendroglia by both RT-PCR and flow cytometry (data not shown). On the other hand, the inventors cannot exclude the possibility that the putative ligand for FcγRs is not an immunoglobulin. However, as demonstrated by the administration of the antibody to FcRγ (FIG. 4), the stimulatory role of FcRγ itself in myelinogenesis suggests the practicable feasibility that this mechanism can in the future promote remyelination.

The expression of exon 2-containing MBP was detected within MS lesions in which a certain degree of remyelination had proceeded (68). The activation of FcRγ resulted in an up-regulation of exon 2-containing MBP levels, and dramatic morphological differentiation (FIG. 4). Taken in conjunction with the reportedly abundant but quiescent immature oligodendroglial population that remained within chronic MS lesions (4), a deeper understanding by the inventors of the initiation of myelinogenesis may provide encouraging future therapeutic strategies for the treatment and prevention of MS and other demyelinating diseases.

In conclusion, the observations of the inventors show that the CNS myelinogenesis is triggered by FcRγ and this uncovers a new connection between the brain and the immune system.

REFERENCES AND NOTES

1) I. Griffiths et al., *Science* 280, 1610 (1998).
2) X. Yin et al., *J. Neurosci.* 18, 1953 (1998).
3) J. H. Noseworthy, *Nature* 399, A40 (1999).
4) G. Wolswijk, *J. Neurosci.* 18, 601 (1998).
5) F. X. Omlin, H. D. Webster, C. G. Palkovits, S. R. Cohen, *J. Cell Biol.* 95, 242 (1982).
6) J. Nakahara et al., *Neurosci. Lett.* 298, 163 (2001).

7) A. Roach, N. Takahashi, D. Pravtcheva, F. Ruddle, L. Hood, Cell 42, 149 (1985).
8) B. Allinquant, S. M. Staugaitis, D. D'Urso, D. R. Colman, *J. Cell Biol.* 113, 393 (1991).
9) H. Umemori, S. Sato, T. Yagi, S. Aizawa, T. Yamamoto, *Nature* 367, 572 (1994).
10) H. Umemori et al., *J. Neurosci.* 19, 1393 (1999).
11) C. Seiwa, I. Sugiyama, T. Yagi, T. Iguchi, H. Asou, *Neurosci. Res.* 37, 21 (2000).
12) U. Bartsch, F. Kirchhoff, M. Schachner, J. Comp. *Neurol.* 284, 451 (1989).
13) R. Sadoul, T. Fahrig, U. Bartsch, M. Schachner, *J. Neurosci. Res.* 25, 1 (1990).
14) C. Li et al., *Nature* 369, 747 (1994).
15) D. Montag et al., *Neuron* 13, 229 (1994).
16) M. D. Weiss, J. Hammer, R. H. Quarles, *J. Neurosci. Res.* 62, 772 (2000).
17) M. Schachner, U. Bartsch, *Glia* 29, 154 (2000).
18) K. Biffiger et al., *J. Neurosci.* 20, 7430 (2000).
19) D. J. Osterhout, A. Wolven, R. M. Wolf, M. D. Resh, M. V. Chao, *J. Cell Biol.* 145, 1209 (1999).
20) A. Niehaus, J. Stegmiller, M. Diers-Fenger, J. Trotter, *J. Neurosci.* 19, 4948 (1999).
21) M. J. Wilson, J. A. Lindquist, J. Trowsdale, *Immunol. Res.* 22, 21 (2000).
22) T. R. Hurley, R. Hyman, B. M. Sefton, *Mol. Cell. Biol.* 13, 1651 (1993).
23) M. Jacobsen et al., *Nat. Genet.* 26, 495 (2000).
24) M. Reth, *Nature* 338, 383 (1989).
25) J. V. Revetch, *Cell* 78, 553 (1994).
26) M. Iwashima, B. A. Irving, N. S. C. Van Oers, A. C. Chan, A. Weiss, *Science* 263, 1136 (1994).
27) L. S. Quek et al., *Blood* 15, 4246 (2000).
28) K. Itoh, Y. Sakurai, H. Asou, H. Umeda, *J. Neurosci. Res.* 60, 579 (2000).
29) Itoh's method detailing the culture: conditions for rat oligodendroglial precursor cells (28) has been adapted for mouse oligodendroglial precursor cells derived from day 17 embryos (courtesy of Chika Seiwa, Dept. of Neurobiology, Tokyo Metropolitan Institute of Gerontology). Approximately 90% of cultured cells were routinely positive for an OPC lineage-specific marker, A2B5 (Chemicon; sold by Funakoshi in Japan) (see 69).
30) H. Asou, K. Murakami, M. Toda, K. Uyemura, Keio *J Med.* 44, 47 (1995).
31) Total RNA was extracted from cultured OPC with Trizol reagent (GIBCO BRL). RNA was resuspended in 20 µl TE. For each sample, 1 µl of RNA was reverse-transcribed, using a first strand cDNA synthesis kit (Boehringer Mannheim) to achieve a final volume of 20 µl. For standardization, mouse β-actin was amplified in parallel. An annealing temperature of 52 degrees was used for the amplification of mouse FcRγ, CD3ζ, FcεRIα, FcγRIα, and β-actin. An annealing temperature of 53 degrees was used for the amplification of FcγRIIIα and FcγRIIb. cDNA samples were amplified for 35 cycles (30 sec at 94 degrees, 30 sec for annealing, and 30 sec at 72 degrees). The following primers were used:
FcRγ sense, 5'-ctcaagatccaggtccga-3' (SEQ ID NO: 1);
FcRγ antisense, 5'-ctactggggtggtttttcat-3' (SEQ ID ND: 2);
CD3ζ sense, 5'-aggcacagagctttggtct-3' (SEQ ID NO: 3);
CD3ζ antisense, 5'-ctggtaaaggccatcgtgc-3' (SEQ ID NO: 4);
FcεRIα sense, 5'-aaatgaactctactactaaa-3' (SEQ ID NO. 5);
FcεRIα antisense 5'-cttttactacagcaattctgaa-3' (SEQ ID NO: 6);
FcγRIα sense, 5'-gaacagccgttcagatct-3' (SEQ ID NO: 7);
FcγRIα antisense, 5'-ttcgtctcacagttcagg-3' (SEQ ID NO: 8);
FcγRIIα sense, 5'-ctaaggtgccatagctgcagg-3' (SEQ ID NO; 9);
FcγRIIIα antisense, 5'-ctgattgacagggacttcctc-3' (SEQ ID NO: 10);
FcγRIIB sense, 5'-gtgaggtatcatcactacagt-3' (SEQ ID NO: 11);
FcγRIIB antisense, 5'-ggttctggtaatcatgctctg-3' (SEQ ID NO 12);
β-actin sense, 5'-tggtcgtcgacaacggct-3' (SEQ ID NO: 13); and
β-actin antisense 5'-tttacggatgtcaacgtcac-3' (SEQ ID NO: 14).
32) G. S. Huh et al., *Science* 290, 2155 (2000).
33) M. C. Raff, R. H. Miller, M. Noble, *Nature* 303, 390 (1983).
34) I. Sommer, M. Schachner, *Dev. Biol.* 83, 311 (1981).
35) Cultured OPC and immature oligodendroglia (courtesy of Chika Seiwa, Dept. of Neurobiology, Tokyo Metropolitan Institute of Gerontology) were fixed with PLP for 15 min at room temperature, followed by an incubation with the primary antibody (overnight at 4 degrees). Then, the cells were stained with the secondary antibody (1.5 hrs at room temperature). In double-staining, cells were stained with different sets of antibodies, following the same protocol.
36) The following antibodies were used in this study. The primary Ab, O1 and O4 mouse monoclonal Ab (34: Chemicon; sold by Funakoshi in Japan), A2B5 mouse monoclonal Ab (33: Chemicon; sold by Funakoshi in Japan), anti-FcRγ rabbit polyclonal Ab (58: courtesy of Pro. T. Takagi, Dept. of Experimental Immunology, Institute of Development, Aging and Cancer, Tohoka University), anti-MBP rabbit polyclonal Ab (Nichirei), anti-MAG rabbit polyclonal Ab (courtesy of the late Dr. Y. Matsuda, National Center for Neurology and Psychiatry, Japan), anti-GFAP rabbit polyclonal Ab (DAKO), Ox-42 mouse monoclonal Ab (43): Serotech), anti-PLP rabbit polyclonal antibody (Sigma), anti-PDGFαR rabbit polyclonal antibody (UBI), anti-m-Msi-1 rat monoclonal antibody (courtesy of Prof. H. Okano, Dept. of Physiology, Keio University School of Medicine, Japan), anti-CNPase mouse monoclonal Ab (sigma) and anti-CD45 rat monoclonal Ab (clone: 30-F11; PharMingen) were used. For immunohistochemistry, HRP-conjugated anti-rabbit-IgG Ab (MBL), HRP-conjugated anti-mouse-IgG Ab (MBL), and biotin-conjugated anti-rat-IgG Ab (DAKO) together with HRP-conjugated streptavidin (Nichirei) were used as secondary antibodies. For immunocytochemisty, rhodamine-conjugated anti-mouse IgM Ab (EY Labo. Inc.) and fluorescein-conjugated anti-rabbit IgG Ab (Cappel) were used as secondary antibodies.
37) 7 culture O4-positive immature oligodendroglia (courtesy of T. Kaifu, Dept. of Experimental Immunology, Institute of Development, Aging and Cancer, Tohoku University), the brains of newborn mice were dissected and prepared for separate cultures (70). After 10 days of culture, oligodendroglia, attached to the astrocytic monolayer, were recovered following mechanical dislodging of the cells by orbital shaking. Over 95% of the recovered cells were routinely positive for O4. The remaining astrocyte-rich cell layer was dissociated by trypsin/EDTA. The recovered cells were subjected to immunoblot analysis.
38) Removed brains were fixed overnight in an Acid-Alcohol solution (95% ethanol/5% acetic acid; vol %). Paraffination was performed on the fixed brains by a standard protocol (100% ethanol→methyl benzoate→xylene→xylene-paraffin solution→paraffin; each for 1-2 hrs); then the samples were embedded in paraffin. Embedded brains were sectioned into 10 µm thick slices using a microtome. Slices then underwent a standard protocol for deparaffination (Xylene→100% ethanol→90% ethanol→70% ethanol→PBS). Intracellular peroxide activity was quenched with 3% H2O2 at room temperature for 10 min. Following an additional rinse with PBS, sections were incubated with a primary antibody either for overnight at 4 degrees or for 2 hrs at 37 degrees, depending on the antibody used. After incubation, slices were washed several times with PBS, then incubated with an appropriate secondary antibody for 1 hr at 37 degrees. For those samples using a biotin-conjugated secondary Ab, slices were also incubated with HRP-conjugated streptavidin (Nichirei) for 30 min at 37 degrees. Following thorough washing with PBS, samples were stained in a solution containing DAB: (Wako). Methyl green (Wako) was used as a counter-stain.

39) Wild type (C57BL/6; Saitama Experimental Animal) mouse FcRγ-deficient mouse (58: courtesy of Prof. T. Takai, Dept. of Experimental Immunology, Institute of Development, Aging and Cancer, Tohoku University), Fyn-deficient mouse (46: courtesy of Prof. Yagi, Institute for Molecular and Cellular Biology, Osaka University), and MBP-deficient mouse (also known as Shiverer mouse; Jackson Lab.) were sacrificed under appropriate anesthesia at all ages tested and there brains were then removed. The backgrounds of all mice, including the mutants, are C57BL/6.

40) S. W. Levison, J. E. Goldmari, *Neuron* 10, 201 (1993).

41) S. Sakakibara, H. Okano, *J. Neurosci.* 17, 8300 (1997).

42) After the preliminary staining, slices were washed several times with PBS. Washing in 0.1 M glycine-HCl buffer (pH 2.2) for 1 hr at room temperature removed the primary antibody. These staining conditions were used for staining with the secondary antibody as well. Following the final stain, a solution containing 4-chloro-1-naphthol (Wako) was used to visualize the secondary antibody.

43) A. P. Robinson, T. M. White, D. W. Mason, *Immunology* 57, 239 (1986).

44) In order to verify the specificity of the anti-MAG sera used, slices of brains afflicted with experimental autoimmune encephalomyelitis (EAE) were stained with the same antibody and the possibility for cross-reactivity of the antibody with a population of FcRγ-bearing immune cells that would be able to exist within the CNS was investigated. The antibody did not react with immune cells invasive into EAE brains (data not shown). The antibody was thus shown to have no cross-reactivity with immune cells.

45) F. Doetsch, I. Caillé, D. A. Lim, J. M. Garcia-Verdugo, A. Alvarez-Buylla, *Cell* 97, 703 (1999).

46) T. Yagi et al., *Nature* 366, 742 (1994).

47) 35 mm dishes, seeded with $1\times10^6$ oligodendroglial precursor cells per dish, were treated with either poly-L-lysine (100 μg/ml; Sigma) alone, poly-L-lysine plus an anti-FcRγ rabbit polyclonal Ab (70 μg/ml), or poly-L-lysine and an anti-FcεRIα mouse monoclonal antibody (clone CRA-1, subtype IgG2b; 20 μg/ml, Kyokuto). Cells were harvested after 24 hrs (FIG. 5A). Following cell lysis with lysis buffer (50 mM Tris-HCl (pH 7.4), 1% NP40, 0.25% sodium deoxycholate, 150 mM NaCl, 1 mM EDTA-2Na, 1 mM $Na_3VO_4$, 1 mM NaF, 1 mM PMSF, 1 μg/ml aprotinin, 1 μg/ml leupeptin, and 1 μg/ml pepstatin), SDS-PAGE was performed on the cell lysates. Gels were processed for Western blotting analysis, using a standard protocol. The CRA-1 antibody would not react with oligodendroglial proteins and this was confirmed by flow cytometry before it was used.

48) The precise methods for the preparation of myelin fractions, SDS-PAGE, and blotting have been described by the present inventors previously (11).

In FIG. 5B, equal quantities of samples as obtained from the myelin-containing fractions of brains from wild type and mutant animals were loaded in individual lanes.

49) F. de Ferra et al., *Cell* 43, 721 (1985).

50) L. Pedraza, L. Fidler, S. M. Staugaitis, D. R. Colman, *Neuron* 18, 579 (1997).

51) S. M. Thomas, J. S. Brugge, *Annu. Rev. Cell. Dev. Biol.* 13, 513 (1997).

52) B. R. sperber et al., *Neurosci.* 21, 2039 (2001).

53) C. Mathis, C. Hindelang, M. LeMeur, E. Borrelli, *J. Neurosci.* 20, 7698 (2000).

54) Quantitation of blotting data was performed using Kodak ID Image Analysis Software, EDAS290 (ver. 3.5).

55) After staining with an anti-MAG Ab, the inventors counted the MAG-positive immature oligodendroglia (6) within the cerebral cortex of both mutant and wild type mice for three slices in each animal. The location within the brain under test matched the anatomical criteria for all animals examined. The means and standard deviations were calculated and graphed.

56) N. P. Pringle, H. S. Mudbar E. J. Collarini W. D. Richardson, *Development* 115, 535 (1992).

57) Fixation for electron microscopic analysis was performed as described elsewhere (51). Ultra-thin sections stained with 2% uranylacetate and leaded solution were observed with a JEOL 100C electron microscope (Nippon Kohden) operated at 80 kV.

58) T. Takai, M. Li, D. Sylvestre, R. Clynes, J. V. Ravetch, *Cell* 76, 519 (1994).

59) N. E. Simister, in *Immunoglobulin Receptors and Their Physiological and Pathological Roles in Immunity*, J. G. J. van de Winkel, P. M. Hogarth Eds. (Kluwer Academic Publishers, Netherlands 1998), pp. 63-71.

60) S. Haba, A. Nisonoff, *Proc. Natl. Acad. Sci.* 89, 5185 (1992).

61) M. L. Thomas, *Curr. Opin. Immunol.* 11, 270 (1999).

62) M. Stangel, K. Toyka, R. Gold, *Arch. Neurol.* 56, 661 (1999).

63) F. Fazekas et al., *Lancet* 349, 589 (1997).

64) M. Rodriguez, V. A. Lennon, *Ann. Neurol.* 27, 12 (1990).

65) F. Miyagi et al., *J. Neuroimmunol.* 78, 127 (1997).

66) K. M. Myhr, G. Raknes, H. Nyland, C. Vedeler, *Neurology* 52, 1771 (1999).

67) M. Da?ron, Fc receptor biology. *Ann. Rev. Immunol.* 15, 203-234 (1997).

68) E. Capello, R. R. Voskuhl, H. F. McFarland, C. S. Raine, *Ann. Neurol.* 41, 797 (1997).

69) Y. Nakai et al., *J. Neurosci. Res.* 62, 521 (2000).

70) K. D. McCarthy, J. de Vellis, *J. Cell Biol.* 85, 890 (1980).

All publications, patents and patent applications cited herein are incorporated herein by reference in their entity.

INDUSTRIAL APPLICABILITY

The pharmaceutical compositions and agents of the present invention are capable of stimulating the differentiation of oligodendroglial precursor cells. The Pharmaceutical compositions and agents of the present invention are also capable of increasing the expression of Fyn tyrosine kinase. Further, the pharmaceutical compositions and agents of the present invention are capable of stimulating the expression of myelin basic protein.

The pharmaceutical compositions and agents of the present invention are useful in stimulating myelinogenesis.

The pharmaceutical compositions and agents of the present invention are useful in preventing and/or treating at least one disease selected from the group consisting of demyelinating diseases, dysmyelinating diseases and myelinoclasis.

In the future, therapeutic treatments will be practiced in which neural stem cells, ES cells or subject-derived oligodendroglia is transplanted and regenerated. When such treatments have become possible, the technique of the present invention will be applicable as a booster for myelinogenesis.

According to the present invention, a method of using FcRγ as a marker for oligodendroglia or precursor cells thereof is provided. FcRγ-positive oligodendroglia can be regarded as cells having the potential of myelinogenesis.

SEQUENCE LISTING FREE TEXT

SEQ ID NO: 1 shows the nucleotide sequence of FcRγ sense primer.

SEQ ID NO: 2 shows the nucleotide sequence of FcRγ antisense primer.

SEQ ID NO: 3 shows the nucleotide sequence of CD3ζ sense primer.

SEQ ID NO: 4 shows the nucleotide sequence of CD3ζ antisense primer.

SEQ ID NO: 5 shows the nucleotide sequence of FcεRIα sense primer.

SEQ ID NO: 6 shows the nucleotide sequence of FcεRIα antisense primer.

SEQ ID NO: 7 shows the nucleotide sequence of FcγRIα sense primer.

SEQ ID NO: 8 shows the nucleotide sequence of FcγRIα antisense primer.

SEQ ID NO: 9 shows the nucleotide sequence of FcγRIIIα sense primer.

SEQ ID NO: 10 shows the nucleotide sequence of FcγRIIIα antisense primer.

SEQ ID NO: 11 shows the nucleotide sequence of FcγRIB sense primer.

SEQ ID NO: 12 shows the nucleotide sequence of FcγRIIB antisense primer.

SEQ ID NO: 13 shows the nucleotide sequence of β-actin sense primer.

SEQ ID NO: 14 shows the nucleotide sequence of β-actin antisense primer.

SEQ ID NO: 15 shows the nucleotide sequence of human FcRγ-mRNA.

SEQ ID NO: 16 shows the amino acid sequence encoded by the nucleotide sequence of human FcRγ-mRNA as shown in SEQ ID NO: 15.

SEQ ID NO: 17 shows the nucleotide sequence of mouse FcRγ-mRNA.

SEQ ID NO: 18 shows the amino acid sequence encoded by the nucleotide sequence of mouse FcRγ-mRNA as shown in SEQ ID NO: 17.

The invention claimed is:

1. A method for inducing or stimulating myelinogenesis in a subject in need thereof, comprising:
   administering to said subject,
   an isolated or purified antibody that binds via an Fab antigen binding site to the gamma (γ) subunit of an Fc receptor (FcRγ) in oligodendroglia or
   an isolated or purified antibody fragment that binds via an Fab antigen binding site to the gamma (γ) subunit of an Fc receptor (FcRγ) in oligodendroglia;
   wherein said binding occurs in an amount sufficient to induce or stimulate myelinogenesis in said subject and reduce the severity of a dysmyelinating or a demyelinating disease.

2. The method of claim 1, wherein an amount of said antibody is administered that stimulates the differentiation of oligodendroglial precursor cells in said subject.

3. The method of claim 1, wherein an amount of said antibody is administered that activates Fyn tyrosine kinase in said subject.

4. The method of claim 1, wherein an amount of said antibody is administered that stimulates the expression of myelin basic protein.

5. The method of claim 1, wherein said subject is a human.

6. The method of claim 1, wherein said subject human and has a demyelinating disease.

7. The method of claim 1, wherein an antibody is administered.

8. The method of claim 1, wherein an antibody fragment is administered.

9. The method of claim 1, wherein the antibody or antibody fragment binds to FcγRI.

10. The method of claim 1, wherein the antibody or antibody fragment binds to FcγRIII.

11. The method of claim 1, wherein the antibody or antibody fragment is IgG or a fragment of IgG.

12. The method of claim 1, wherein the antibody or antibody fragment is murine IgG2a, IgG1, IgG2b or IgG3.

13. The method of claim 1, wherein the antibody or antibody fragment is human IgG3, IgG1, IgG4 or IgG2.

14. The method of claim 1, wherein the antibody or antibody fragment is a chimeric or humanized antibody or chimeric or humanized antibody fragment.

15. The method of claim 1, wherein the antibody or antibody fragment is administered in combination with a pharmaceutically acceptable carrier, diluent or exicipient.

16. The method of claim 1, wherein the subject is human, and the antibody or antibody fragment is administered in an amount ranging from 150-500 mg/kg body weight.

17. The method of claim 1, wherein the antibody or antibody fragment is administered intravenously.

18. The method of claim 1, wherein said subject human and has a dysmyelinating disease.

19. The method of claim 18, wherein said subject is human and the dysmyelinating disease is multiple sclerosis.

* * * * *